US010201198B2

(12) United States Patent
Tong et al.

(10) Patent No.: US 10,201,198 B2
(45) Date of Patent: Feb. 12, 2019

(54) PROTECTIVE MASKS WITH COATING COMPRISING DIFFERENT ELECTROSPUN FIBERS INTERWEAVED WITH EACH OTHER, FORMULATIONS FORMING THE SAME, AND METHOD OF PRODUCING THEREOF

(71) Applicant: Profit Royal Pharmaceutical Limited, Hong Kong (HK)

(72) Inventors: Ho Wang Tong, Hong Kong (HK); Sau Kuen Connie Kwok, Hong Kong (HK); Hang Ching Kwok, Hong Kong (HK)

(73) Assignee: Profit Royal Pharmaceutical Limited, Hong Kong (HK)

( * ) Notice: Subject to any disclaimer, the term of this patent is extended or adjusted under 35 U.S.C. 154(b) by 505 days.

(21) Appl. No.: 14/964,593

(22) Filed: Dec. 10, 2015

(65) Prior Publication Data

US 2016/0174631 A1   Jun. 23, 2016

Related U.S. Application Data

(60) Provisional application No. 62/096,531, filed on Dec. 23, 2014.

(51) Int. Cl.
*A41D 13/11* (2006.01)
*A01N 25/10* (2006.01)
(Continued)

(52) U.S. Cl.
CPC .......... *A41D 13/1192* (2013.01); *A01N 25/10* (2013.01); *A01N 25/34* (2013.01);
(Continued)

(58) Field of Classification Search
CPC ................ A41D 13/11; A41D 13/1146; A41D 13/1184; A41D 13/1161; A41D 13/1192;
(Continued)

(56) References Cited

U.S. PATENT DOCUMENTS 8,303,693 B2   11/2012   Leung
8,523,971 B2   9/2013   Leung et al.
(Continued)

FOREIGN PATENT DOCUMENTS

CN   102499493 A   6/2012
CN   102872653 A   1/2013
(Continued)

OTHER PUBLICATIONS

International Search Report and Written Opinion for corresponding PCT Application No. PCT/CN2015/097936.
(Continued)

*Primary Examiner* — Ophelia A Hawthorne
(74) *Attorney, Agent, or Firm* — Spruson & Ferguson (Hong Kong) Limited

(57) ABSTRACT

The present invention provides a protective mask with an ultrafine fibrous coating. The ultrafine fibrous coating includes partially gelled submicron fibers interweaved with nanofibers and a biocide encapsulated in, surface-attached onto, blended with, physically trapped, and/or chemically linked to the submicron fibers and nanofibers. In an example, a microfibrous substrate with the coating assembles with other microfibrous substrates to form a protective mask having N95 level of protection and bacteria-killing capability.

20 Claims, 11 Drawing Sheets

(51) Int. Cl.
    *C09D 5/14*     (2006.01)
    *C09D 175/04*     (2006.01)
    *A01N 25/34*     (2006.01)

(52) U.S. Cl.
    CPC .............. *C09D 5/14* (2013.01); *C09D 175/04* (2013.01); *A41D 13/11* (2013.01)

(58) Field of Classification Search
    CPC ....... A62B 23/025; A62B 23/02; A62B 18/08; B01D 46/0028; B01D 39/1623; B01D 46/0036; B01D 46/10; B01D 2239/025; B01D 2239/0258; B01D 2239/0442; B01D 2239/065; B01D 2275/10; Y10T 29/49801

See application file for complete search history.

(56) References Cited

U.S. PATENT DOCUMENTS

| | | | |
|---|---|---|---|
| 2010/0313890 | A1 | 12/2010 | Messier |
| 2012/0082711 | A1 | 4/2012 | Goranov |
| 2013/0180917 | A1 | 7/2013 | Chu et al. |
| 2014/0026897 | A1 | 1/2014 | Saroch et al. |
| 2014/0097558 | A1 | 4/2014 | Lustenberger |
| 2014/0242148 | A1 | 8/2014 | Whitten |

FOREIGN PATENT DOCUMENTS

| | | |
|---|---|---|
| CN | 102920067 A | 2/2013 |
| CN | 203467710 U | 3/2014 |
| CN | 103726224 A | 4/2014 |
| CN | 104305591 A | 1/2015 |
| WO | 2014141039 A1 | 9/2014 |

OTHER PUBLICATIONS

Atrie and Worster, "Surgical mask versus N95 respirator for preventing influenza among health care workers: a randomized trial", CJEM 2012;14(1):50-52.

Baig et al., "Health care workers' views about respirator use and features that should be included in the next generation of respirators", Am J Infect Control 2010;38:18-25.

Eck and Vannier, "The Effect of High-Efficiency Particulatea Irrespirator Design on Occupational Health: A Pilot Study Balancing Risks in the Real World", Infection Control and Hospital Epidemiology, vol. 18, No. 2 (Feb. 1997), pp. 122-127.

Lau et al., "SARS Transmission among Hospital Workers in Hong Kong", Emerging Infectious Diseases, vol. 10, No. 2 (Feb. 2004), pp. 280-286.

Lu et al., "Viral Load and Outcome in SARS Infection: The Role of Personal Protective Equipment in the Emergency Department", The Journal of Emergency Medicine, vol. 30, No. 1, pp. 7-15, 2006.

Moore et al., "Occupational Health and Infection Control Practices Related to Severe Acute Respiratory Syndrome: Health Care Worker Perceptions", AAOHN J. Jun. 2005;53(6):257-66.

Nishiyama et al., "Risk factors for SARS infection within hospitals in Hanoi, Vietnam", Jpn J Infect Dis. Sep. 2008;61(5):388-90.

Radonovich et al., "Respirator Tolerance in Health Care Workers", JAMA. Jan. 7, 2009;301(1):36-38.

Yen et al., "Using an integrated infection control strategy during outbreak control to minimize nosocomial infection of severe acute respiratory syndrome among healthcare workers", Journal of Hospital Infection (2006) 62, 195-199.

Supplementary European Search Report and European Search Opinion of EP application No. 15871916.1 issued from the European Patent Office dated Apr. 20, 2018.

Third Office Action from the State Intellectual Property of the PRC dated Apr. 27, 2018.

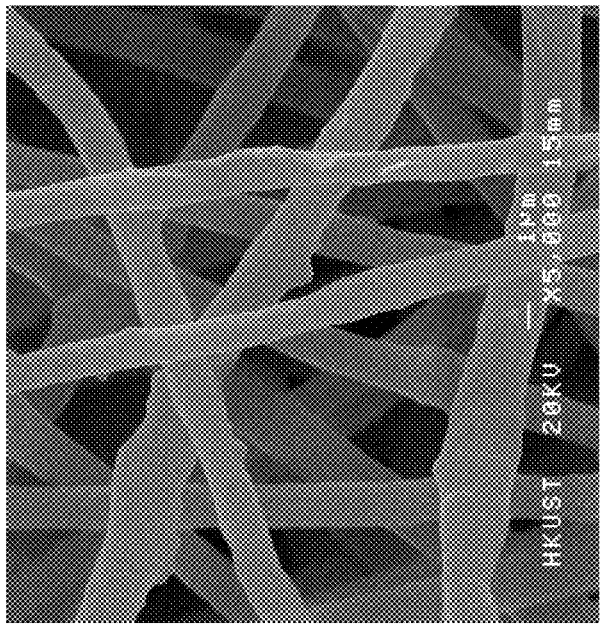
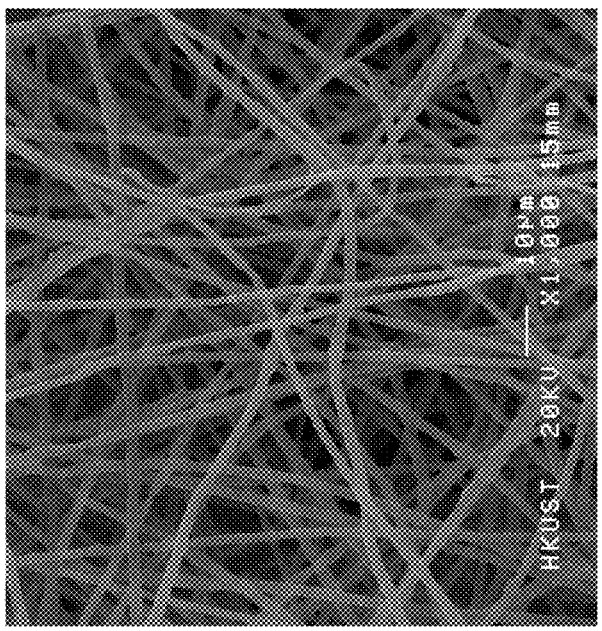
FIG. 7

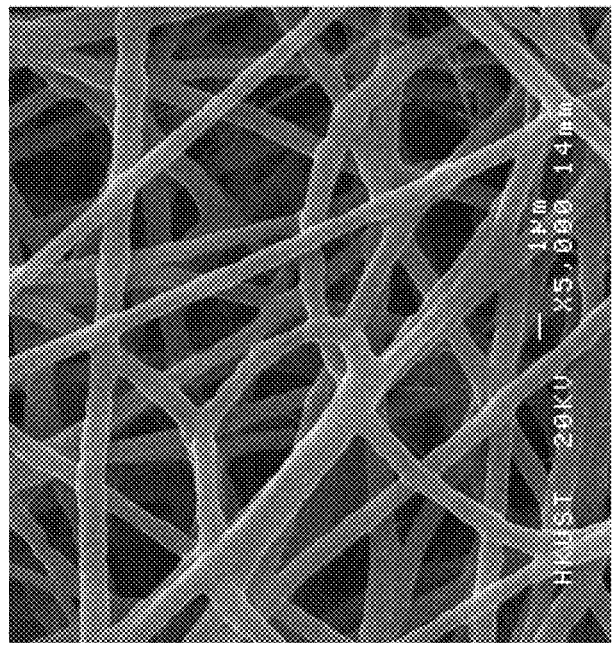
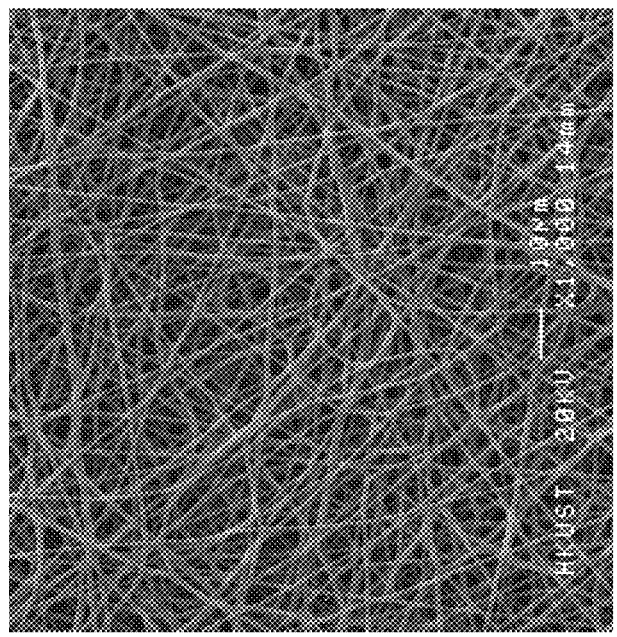
FIG. 8

PROTECTIVE MASKS WITH COATING COMPRISING DIFFERENT ELECTROSPUN FIBERS INTERWEAVED WITH EACH OTHER, FORMULATIONS FORMING THE SAME, AND METHOD OF PRODUCING THEREOF

CROSS-REFERENCE TO RELATED APPLICATIONS

This application claims priority from the U.S. provisional patent application Ser. No. 62/096,531 filed Dec. 23, 2014, and the disclosure of which is incorporated herein by reference in its entirety

TECHNICAL FIELD

The present invention relates to protective masks based on partially gelled submicron fibers and nanofibers. In particular, the present invention relates to protective masks based on partially gelled submicron fibers which are interweaved with nanofibers in order to form said protective masks. The present invention also relates to a method of making the protective masks and coatings therein and related formulation forming the coatings.

BACKGROUND OF THE INVENTION

Hazards of Airborne Contaminants

Airborne contaminants are present everywhere in the surrounding. In hospitals, contaminants include a variety of airborne respiratory infectious diseases, such as tuberculosis and measles, and emerging diseases such as severe acute respiratory syndrome (SARS) and H1N1 influenza A. In highly polluted areas, aerosol, which is suspension of solid or liquid particles in gas, becomes the major airborne contaminant.

Absorption of airborne contaminants of high concentrations into the body can be potentially very dangerous. Airborne contaminants can be absorbed into the body through skin, eyes, or the respiratory system. Absorption of airborne particles into lungs through the respiratory system is prone to both acute and chronic health hazards.

When it comes to the harmful effects of contaminants on human respiratory system, the size of the contaminants is important. In general, smaller particles are more likely to become airborne and more dangerous. Particles larger than 10 μm usually get collected in upper part of the respiratory system. Therefore, most of them cannot get into the deep part of the lungs. However, particles smaller than 10 μm are respirable, which means that they are capable of getting into the deep part of the lungs. Those particles include but not limited to bacteria, viruses, clay, silt, tobacco smoke and metal fumes. They seem to have the unexplained ability to rapidly penetrate cells throughout the body and impair many cellular functions.

Protection Against Airborne Contaminants Using Protective Masks

The hazard of airborne contaminants can be managed through the application of basic controls like increasing ventilation, or providing workers with protective equipment such as protective masks.

Protective masks have been widely used by personnel in hospitals, researchers in laboratories, workers in construction sites, as well as the general public in highly polluted areas or during flu season.

According to the Centers for Disease Control and Prevention (CDC), flu viruses are spread mainly by droplets made when people with the flu cough, sneeze or talk. These droplets can land in the mouths or noses of people who are nearby or possibly be inhaled into the lungs. According to the CDC, a person might also get the flu by touching a surface or object that has the flu virus on it and then touching his/her own mouth or nose.

A protective mask is typically composed of a filtering barrier, which is a critical component that determines the protection level of the mask.

For the same filtering barrier, the filtration efficiency depends on the particle size and the rate of airflow. Generally, it is relatively ineffective for a filtering barrier used in the conventional protective mask to filter out particles having sizes at around 0.3 μm and it is more difficult to filter out particles when the rate of airflow is high.

Most filtering barriers of the conventional protective masks are not functionalized with biocides or virucides. Therefore, those protective masks simply serve as a physical barrier to filter out contaminants. When it comes to viruses and bacteria, those barriers cannot kill them on the spot. The ability to kill bacteria and/or viruses on the spot is a desirable function for protective masks.

Different Types of Protective Masks

Although there are many different types of protective masks on the market, surgical/medical masks and N95 respirators are two of the most popular masks. These masks have remained virtually unchanged for the last several decades. Studies of surgical/medical masks and N95 respirators in terms of their levels of protection and general comfort have been reported (Atrie, D. and A. Worster, *Surgical mask versus N95 respirator for preventing influenza among health care workers: A randomized trial*. Canadian Journal of Emergency Medicine, 2012. 14(1): p. 50-52; Baig, A. S., et al., *Health care workers' views about respirator use and features that should be included in the next generation of respirators*. American Journal of Infection Control, 2010. 38(1): p. 18-25).

Whether the goal is to prevent the outward escape of wearer-generated contaminants or the inward transport of hazardous aerosols, there are two critical requirements to justify the protection level of a mask. Firstly, the filter of the mask must be able to prevent penetration of hazardous particles within a wide range of sizes (from a few nanometers to a few hundred micrometers) over a range of airflow (approximately 10 to 100 L/min). Secondly, leakage must be avoided at the boundary of the mask and the face. Both requirements (i.e. well-functioning filter and good face seal performance) must be met in order to claim a mask highly protective.

Different types of the conventional protective masks, including (1) surgical/medical mask, (2) respirator, (3) protective mask with filtering face seal, and (4) antibacterial/antiviral mask, are described below, respectively.

(1) Surgical/Medical Mask

In order to claim a product as a surgical/medical mask, the product must pass a series of tests according to the standard such as ASTM F2100 or EN14683.

For ASTM F2100, the performance of a surgical/medical mask is based on testing for (1) bacterial filtration efficiency (BFE), (2) differential pressure, (3) sub-micron particulate filtration efficiency (PFE), (4) resistance to penetration tested by synthetic blood, and (5) resistance to flammability.

The table below summarizes the surgical/medical mask requirements by performance level according to ASTM F2100.

| | | Requirements | | |
|---|---|---|---|---|
| | Tests | Level 1 Barrier | Level 2 Barrier | Level 3 Barrier |
| (1) | BFE at 28.3 L/min (challenge used: *Staphylococcus aureus*, with a mean size at around 3 μm) | >=95% | >=98% | >=98% |
| (2) | Differential pressure at 8 L/min | <4.0 mm $H_2O/cm^2$ | <5.0 mm $H_2O/cm^2$ | <5.0 mm $H_2O/cm^2$ |
| (3) | Sub-micron PFE at 28.3 L/min (challenge used: 0.1 μm Latex spheres) | >=95% | >=98% | >=98% |
| (4) | Resistance to penetration by synthetic blood, minimum pressure for pass result | 80 mm Hg | 120 mm Hg | 160 mm Hg |
| (5) | Flame spread | Class 1 | Class 1 | Class 1 |

For typical surgical/medical masks, and in referencing to the BFE test and the sub-micron PFE test, the filtration efficiency percentage must not be lower than 95%. The average size of the aerosol particles in the BFE test is around 3 μm while the average size of the aerosol particles in the sub-micron PFE test is around 0.1 μm.

The aerosol particles are trapped by protective masks comprising nonwoven meshes of fibers through a combination of mechanisms including inertial impaction capture, interception capture, and Brownian diffusion capture. Inertial impaction/interception predominates in the BFE test because of the relatively large particle size while Brownian diffusion predominates in the sub-micron PFE test because of the relatively small particle size.

The most penetrating particle size (MPPS) is 0.3 μm. As both diffusion and impaction/interception are inefficient for particles near the MPPS, passing the aforementioned tests (i.e. BFE test and sub-micron PFE test) does not justify the high level of protection of the surgical/medical mask.

Moreover, surgical/medical masks are not designed to seal tightly to the face. Without an adequate seal to the face, inhaled breath is not forced through the filter and instead flows through the gaps around the seal area, providing minimal protection by allowing potentially hazardous contaminants to enter the workers' breathing zone through gaps between the wearer's face and the mask. Therefore, surgical/medical masks do not provide the degree of protection to be considered respiratory personal protective equipment (PPE).

(2) Respirator

When high level of protection is required, respirators are usually used instead of surgical/medical masks. There are nine types of respirator filters, as shown in the table below.

| | | |
|---|---|---|
| N95 | N99 | N100 |
| R95 | R99 | R100 |
| P95 | P99 | P100 |

Respirator filters are rated as N, R or P for their level of protection against oil aerosols. This rating is critical in industry because some industrial oils can remove electrostatic charges from the filter media, thereby reducing the filtration efficiency. Respirators are rated "N" if they are not resistant to oil, "R" if they are somewhat resistant to oil, and "P" if they are strongly resistant to oil.

Respirator filters that capture at least 95% of the challenge aerosol are given a 95 rating. Those that trap at least 99% receive a 99 rating. And those that collect at least 99.97% receive a 100 rating.

N95 respirator is the most popular PPE among the aforementioned respirators. In order to claim a product as an N95 respirator, the product must pass the required National Institute for Occupational Safety and Health (NIOSH) test, which is more stringent than the tests used for surgical/medical masks in terms of protection.

The table below summarizes the N95 respirator requirements by performance level according to NIOSH.

| | Tests | Requirements |
|---|---|---|
| (1) | Filtration efficiency at 85 L/min (challenge used: 0.3 μm NaCl particles) | >=95% |
| (2) | Inhalation resistance at 85 L/min | <=35 mm $H_2O$ |
| (3) | Exhalation resistance at 85 L/min | <=25 mm $H_2O$ |

According to NIOSH, neutralized sodium chloride (NaCl) aerosol comprising particles at the MPPS is used as the challenge. Neutralized aerosol is used to prevent attraction of particles to the sample by electrostatic force. The flow rate of the NaCl aerosol is 85 L/min, which is higher than the flow rate employed in the BFE test (i.e. 28.3 L/min). Such flow rate is also higher than the air requirement for a human under most circumstances such as sitting, walking, and even jogging. The filtration efficiency must not be lower than 95% in order to maintain an N95 rating. Therefore, the N95 respirator is superior to the surgical/medical mask in terms of protective power.

Case control studies during the 2003 SARS crisis also demonstrated that N95 respirators were more protective than surgical/medical masks against the SAR coronavirus (Lau, J. T. F., et al., *SARS transmission among hospital workers in Hong Kong*. Emerging Infectious Diseases, 2004. 10(2): p. 280-286; Lu, Y. T., et al., *Viral load and outcome in SARS infection: the role of personal protective equipment in the emergency department*. The Journal of Emergency Medicine, 2006. 30(1): p. 7-15; Nishiyama, A., et al., *Risk factors for SARS infection within hospitals in Hanoi, Vietnam*. Japanese Journal of Infectious Diseases, 2008. 61(5): p. 388-390; Yen, M. Y., et al., *Using an integrated infection control strategy during outbreak control to minimize nosocomial infection of severe acute respiratory syndrome among healthcare workers*. Journal of Hospital Infection, 2006. 62(2): p. 195-199).

Despite the high level of protection of N95 respirators, many studies of N95 respirators in the US marketplace have shown them to be associated with overall discomfort, diminished visual, vocal, or auditory acuity, excessive humidity or heat, headaches, facial pressure, skin irritation or itchiness, excessive fatigue or exertion, malodorousness, anxiety or claustrophobia, and other interferences with occupational duties (Eck, E. K. and A. Vannier, *The effect of high-efficiency particulate air respirator design on occupational health: a pilot study balancing risks in the real world*. Infection Control and Hospital Epidemiology, 1997. 18(2): p. 122-127; Moore, D. M., et al., *Occupational health and infection control practices related to severe acute respiratory syndrome: health care worker perceptions*. Journal of the American Association of Occuptional Health Nurses, 2005. 53(6): p. 257-266; Radonovich Jr, L. J., et al., *Respirator tolerance in health care workers*. The Journal of the American Medical Association, 2009. 301(1): p. 36-38).

In general, the N95 respirator is inferior to the surgical/medical mask in terms of its breathability. It is relatively comfortable to wear surgical/medical masks when compared with N95 respirators, which provide high level of protection at the expense of breathability. Medical personnel and patients are facing dilemma of choosing a comfortable but unreliable protective mask (i.e. surgical/medical mask) or choosing a highly protective but uncomfortable mask (i.e. N95 respirator). It is desirable to manufacture protective masks that combine the advantage of surgical/medical masks (i.e. low air resistance) and the advantage of N95 respirators (i.e. high protective power).

(3) Protective Mask with Filtering Face Seal

Unlike the traditional N95 respirator that seals to the face and keep air out, the surgical/medical mask does not provide an airtight seal. As such, air can still enter the breathing zone through the top, bottom and sides of the surgical/medical mask without passing through its filter. The absence of the airtight seal gives the wearer the comfort and breathability at the expense of the level of protection. In US20100313890 A1, Messier incorporated the surgical/medical mask with an additional filtering face seal that is designed to filter air before it enters the breathing zone through the top, bottom and sides of the mask. It is believed that the modified mask is more protective than the traditional surgical/medical mask.

(4) Antibacterial/Antiviral Mask

Typical protective masks, including surgical/medical masks and N95 respirators, are usually unable to kill airborne pathogens. These masks provide protection based on a passive, mechanical filtration design. Therefore, microorganisms attached to these masks can survive for several hours. That greatly increases the risk of cross-infection. Functional protective masks capable of not only trapping but also killing microorganisms on the spot are certainly better than most typical masks in terms of protective power.

One of the models of the Gammex® mask (A400) developed by Ansell Healthcare is able to kill microorganisms (e.g. bacteria, viruses, bacterial spores, fungi and protozoa) on the spot. To make the antimicrobial layer, iodine is fused with a polymer under heat and pressure. Incorporation of iodine controls the delivery and dosage of molecular iodine directly to microorganisms, thus providing built-in antimicrobial and antifungal activities.

On the other hand, Filligent Limited developed a functional three-layered protective mask (BioMask™) in 2009. The functional mask is composed of a non-active inner layer made of polypropylene as a supporting layer, a non-active middle layer comprising nonwoven fibers to filter out particulates, and a hydrophilic layer that rapidly inactivates pathogens. Virus-laden droplets are rapidly absorbed and captured within a low pH environment, wherein structural components and proteins are disrupted, and viruses inactivated. The mechanism of action is that the low pH causes non-specific denaturation of viral proteins.

Filligent Limited also developed a functional four-layered protective mask, which is composed of an antimicrobial outer layer, an antimicrobial middle layer, a non-active middle layer and a non-active inner layer. Briefly, viruses are rapidly inactivated in the outer layer by exposure to the low pH environment which causes structural rearrangement of lipids and other structures, resulting in spontaneous denaturation. Positively charged divalent copper/zinc metal ions attach to influenza viruses by binding negatively-charged groups (e.g. carboxyl/sulfhydryl) present on all viruses. This effect is known as ionic mimicry. Influenza viruses are rapidly inactivated because (i) structures, such as lipid envelopes and nucleic acids, are damaged, and (ii) biomolecules, such as proteins, lipids and enzymes, are denatured. The toxic effect of metal ions on pathogens is known as the oligodynamic effect.

Agkilbact™ is an antibacterial mask consisting of 3 layers: (i) the outer polypropylene nonwoven fibrous mesh; (ii) the inner nonwoven mesh comprising silver nanoparticles; (iii) the inner filtering cloth. The antibacterial mask can prevent the growth of various microbes such as extended-spectrum beta-lactamase (ESBL), methicillin-resistant *staphylococcus aureus* (MRSA), and vancomycin-resistant *enterococcus* (VRE). By coating the fibers in the masks with nano functional emulsions, the fibers become hydrophobic, thus preventing absorption and penetration of bacterium-carrying and virus-carrying liquid.

Shortcomings of the Prior Art

To sum up, wearing a surgical/medical mask does not cause significant discomfort generally. However, the protective power of a surgical/medical mask is low because of two reasons. Firstly, the filtration tests for surgical/medical masks do not involve the use of particles at MPPS as the challenge. So its ability to filter out contaminants at a certain range of sizes is not justified. Secondly, contaminants can bypass the filtering material of a surgical/medical mask because air can get into the gap between the surgical/medical mask and the face. On the other hand, respirators such as N95 respirators are highly protective because of their airtight design and the use of particles at MPPS as the challenge during the filtration tests. However, the breathability of N95 respirators is low, leading to low user compliance. And most N95 respirators do not possess antibacterial function. There exists a need for a highly breathable N95 mask capable of trapping viruses and killing bacteria on the spot.

SUMMARY OF THE INVENTION

Accordingly, in a first aspect, the present invention provides formulations and scalable methods for preparing a protective mask that possesses N95 level of protection, high breathability with good face seal, and antibacterial property. In a second aspect, the present invention provides microfibers, submicron fibers and nanofibers made by these formulations and scalable methods. The scalable methods of the present invention can provide for free-surface electrospinning of the present formulations, i.e., biocide-loaded polymer solutions, into microfibers, submicron fibers and nanofibers that can be formed into a coating comprising a plurality of the electrospun microfibers, submicron fibers and/or nanofibers. Said coating can be applied to an antistatic nonwoven substrate comprising a plurality of spunbond microfibers. Non-antistatic nonwoven can also be used but is not preferred in the present invention because it reduces the productivity due to substantial amount of residual charges on the non-antistatic nonwoven. Said coating can also be applied to a nonwoven substrate comprising a plurality of meltblown microfibers. The coating is attached to the nonwoven substrate by mechanical interlocking and/or intermolecular attraction. In a third aspect, the present invention provides a method of using said microfibers, submicron fibers and nanofibers as one or more coatings for the protective mask of the present invention.

The protective mask of the present invention can be foldable or non-foldable. The protective mask can also be butterfly-shaped, cup-shaped or duckbill-shaped.

In one embodiment, the protective mask of the present invention includes a main body, two elastic straps, and preferably a spongy strip attached to the inner part of the main body. The main body includes three to four nonwoven layers, which are attached to each other by ultrasonic welding. A first layer of said three to four nonwoven layers distal to the face of a wearer and a fourth layer proximal to the face of the wearer are nonwoven layers comprising spunbond polypropylene microfibers. One of the first and fourth layers is a nonwoven layer comprising antistatic spunbond polypropylene microfibers with a coating, said coating comprising electrospun microfibers and electrospun nanofibers. The coating is applied to one side of any of the first and fourth layers such that the coating is not exposed to the environment outside the protective mask. The electrospun microfibers and the electrospun nanofibers of said coating can be polymer fibers or biocide-loaded polymer fibers. Between the first layer and the fourth layer are two middle layers (second and third layers). The second or third layer is a nonwoven layer comprising meltblown polypropylene microfibers. In other embodiment, one of the second and third layers can be omitted. A stiffening member such as a metal strip or a plastic strip is attached to the upper edge of the main body to conform the face when wearing the protective mask. Preferably, a spongy strip is attached to the inner part of the main body to further improve the face seal when the wearer is wearing the protective mask.

The elastic straps can be attached to the left hand side of the main body and the right hand side of the main body respectively such that the protective mask can be fixed onto the face with the support from the wearer's ears. The elastic straps can also be attached to the upper side of the main body and the lower side of the main body respectively such that the protective mask can be fixed onto the face with the support from the wearer's head.

The biocide-loaded polymer solution for free-surface electrospinning can include a selected biocide and a selected polymer. The electrospun fibers formed from said biocide-loaded polymer can bear electrostatic charges. The biocide in said biocide-loaded polymer solution and biocide-loaded polymer fibers can include but not limited to silver, copper, copper oxide (CuO), titanium oxide (TiO), zinc oxide (ZnO), iodine, triclosan and chlorhexidine. The biocide can be encapsulated into the electrospun fibers. The biocide can also be surface-attached onto the electrospun fibers. The biocide can be encapsulated into and surface-attached onto the electrospun fibers. The biocide can be physically trapped by the electrospun fibers. The biocide can also be chemically crosslinked to the electrospun fibers. The biocide can also be blended with the electrospun fibers.

The polymer used to form different types of polymer microfibers, submicron fibers and nanofibers of the present invention can include synthetic polymers such as cellulose acetate (CA), polyamide 6 (PA 6), polystyrene (PS), polyacrylonitrile (PAN), polyvinylpyrrolidone (PVP), polyvinyl alcohol (PVA), poly(lactic acid) (PLA), poly(lactic-co-glycolic acid) (PLGA), polybutylene terephthalate (PBT) and polyurethane (PU). The polymer can also include natural polymers such as gelatin, chitosan and polyhydroxybutyrate-co-hydroxyvalerate (PHBV).

These and other examples and features of the present invention and methods will be set forth in part in the following Detailed Description. This Summary is intended to provide an overview of the present invention, and is not intended to provide an exclusive or exhaustive explanation. The Detailed Description below is included to provide further information about the present disclosures and methods.

BRIEF DESCRIPTION OF THE DRAWINGS

FIG. 7 shows the SEM image of electrospun PU/CuO microfibers.

FIG. 8 shows the SEM image of electrospun PU/CuO submicron fibers.

DETAILED DESCRIPTION OF THE INVENTION

Figure 1:
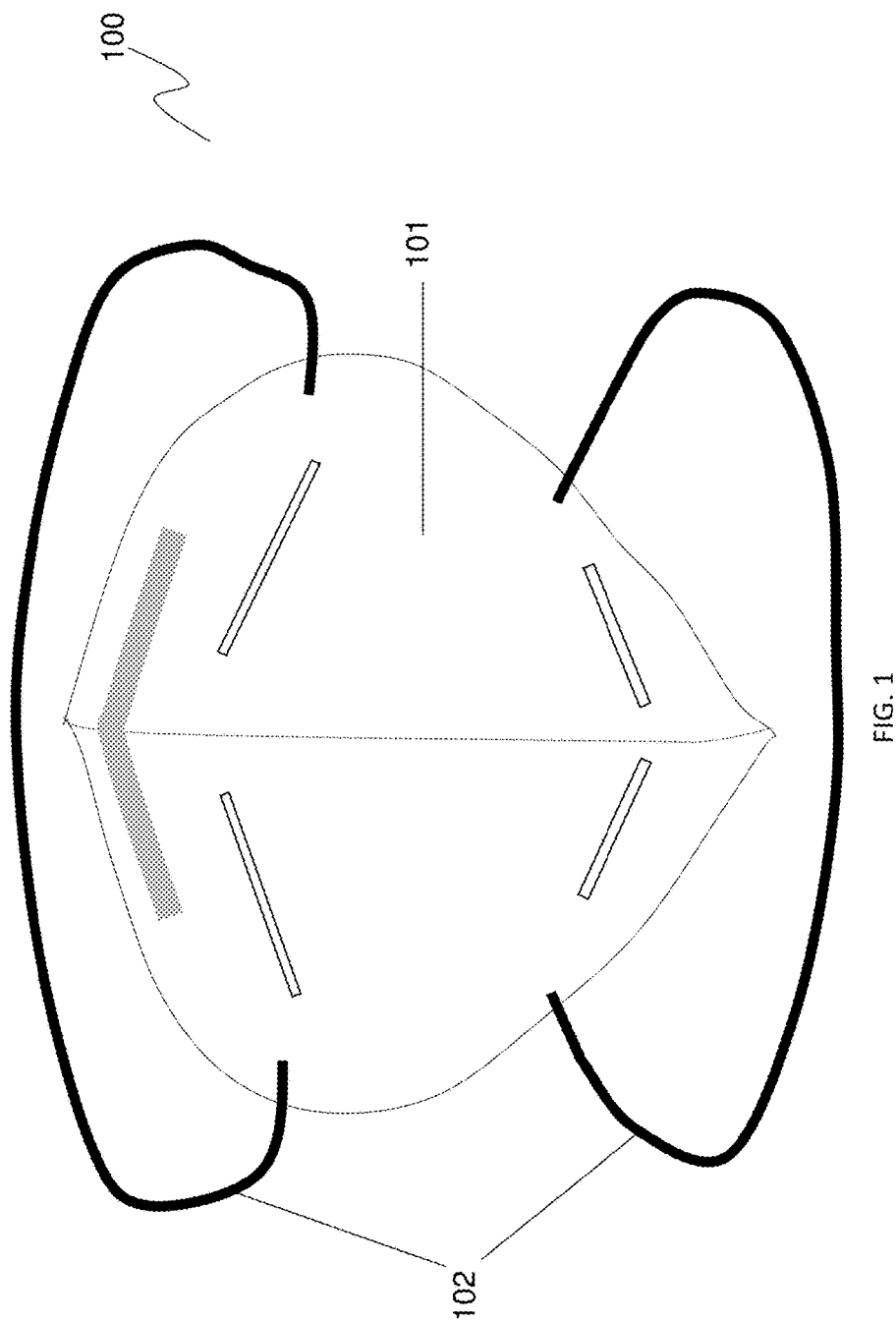
FIG. 1 is a protective mask according to an embodiment of the present invention.

References in the specification to "one embodiment", "an embodiment", "an example embodiment", etc., indicate that the embodiment described can include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a concentration range of "about 0.1% to about 5% should be interpreted to include not only the explicitly recited concentration of about 0.1 wt. % to about 5 wt. %, but also the individual concentrations (e.g., 1%, 2%, 3%, and 4%) and the sub-ranges (e.g., 0.1% to 0.5%, 1.1% to 2.2%, and 3.3% to 4.4%) within the indicated range.

As described herein, the terms "a" or "an" are used to include one or more than one and the term "or" is used to refer to a nonexclusive "or" unless otherwise indicated. In addition, it is to be understood that the phraseology or terminology employed herein, and not otherwise defined, is for the purpose of description only and not of limitation. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods of manufacturing described herein, the steps can be carried out in any order without departing from the principles of the invention, except when a temporal or operational sequence is explicitly recited. Recitation in a claim to the effect that first a step is performed, and then several other steps are subsequently performed, shall be taken to mean that the first step is performed before any of the other steps, but the other steps can be performed in any suitable sequence, unless a sequence is further recited within the other steps. For example, claim elements that recite "Step A, Step B, Step C, Step D, and Step E" shall be construed to mean step A is carried out first, step E is carried out last, and steps B, C, and D can be carried out in any sequence between steps A and E, and that the sequence still falls within the literal scope of the claimed process. A given step or sub-set of steps can also be repeated.

Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

Definitions

The singular forms "a," "an" and "the" can include plural referents unless the context clearly dictates otherwise.

The term "about" can allow for a degree of variability in a value or range, for example, within 10%, or within 5% of a stated value or of a stated limit of a range.

The term "independently selected from" refers to referenced groups being the same, different, or a mixture thereof, unless the context clearly indicates otherwise. Thus, under this definition, the phrase "X1, X2, and X3 are independently selected from noble gases" would include the scenario where, for example, X1, X2, and X3 are all the same, where X1, X2, and X3 are all different, where X1 and X2 are the same but X3 is different, and other analogous permutations.

The term "protective mask" as used herein refers to facemask, face mask, mask, respirator, face shield, surgical mask, medical mask, filter mask, mouth mask, or gas mask.

The term "bacteria" refers to gram-positive bacteria or gram-negative bacteria. Examples of gram-positive bacteria include but not limited to *Staphylococcus aureus, Streptococcus pneumonia*, or Vancomycin-resistant *enterococci* (VRE). Examples of gram-negative bacteria include but not limited to *Pseudomonas aeruginosa, Acinetobacter baumannii*, or *Escherichia coli*.

The term "pore" as used herein refers to a depression, slit, or hole of any size or shape in a solid object. A pore can run all the way through an object or partially through the object. A pore can intersect other pores.

Descriptions

The present invention is not to be limited in scope by any of the following descriptions. The following examples or embodiments are presented for exemplification only.

The present invention describes a protective mask (100) comprising butterfly-shaped main body (101), two elastic straps (102) and preferably a spongy (not shown in FIG. 1) attached to the inner surface of the main body. The main body includes three to four nonwoven layers (FIG. 2), which are attached to each other by ultrasonic welding.

In an example, the present invention provides a protective mask comprising, from distal to the face to proximal to the face, an antistatic spunbond microfibrous nonwoven layer with an electrospun microfibrous coating, a meltblown microfibrous nonwoven layer, and a spunbond microfibrous nonwoven layer.

In another example, the present invention provides a protective mask comprising, from distal to the face to proximal to the face, an antistatic spunbond microfibrous nonwoven layer with an electrospun submicron fibrous coating, a meltblown microfibrous nonwoven layer, and a spunbond microfibrous nonwoven layer.

In another example, the present invention provides a protective mask comprising, from distal to the face to proximal to the face, an antistatic spunbond microfibrous nonwoven layer with an electrospun charge-bearing submicron fibrous coating, a meltblown microfibrous nonwoven layer, and a spunbond microfibrous nonwoven layer.

In another example, the present invention provides a protective mask comprising, from distal to the face to proximal to the face, an antistatic spunbond microfibrous nonwoven layer with an electrospun coating consisting of partially gelled submicron fibers interweaved with nanofibers, a meltblown microfibrous nonwoven layer, and a spunbond microfibrous nonwoven layer.

In yet another example, the present invention provides a protective mask comprising, from distal to the face to proximal to the face, an antistatic spunbond microfibrous nonwoven layer with an electrospun coating consisting of charge-bearing partially gelled submicron fibers interweaved with charge-bearing nanofibers, a meltblown microfibrous nonwoven layer, and a spunbond microfibrous nonwoven layer.

Figure 2:
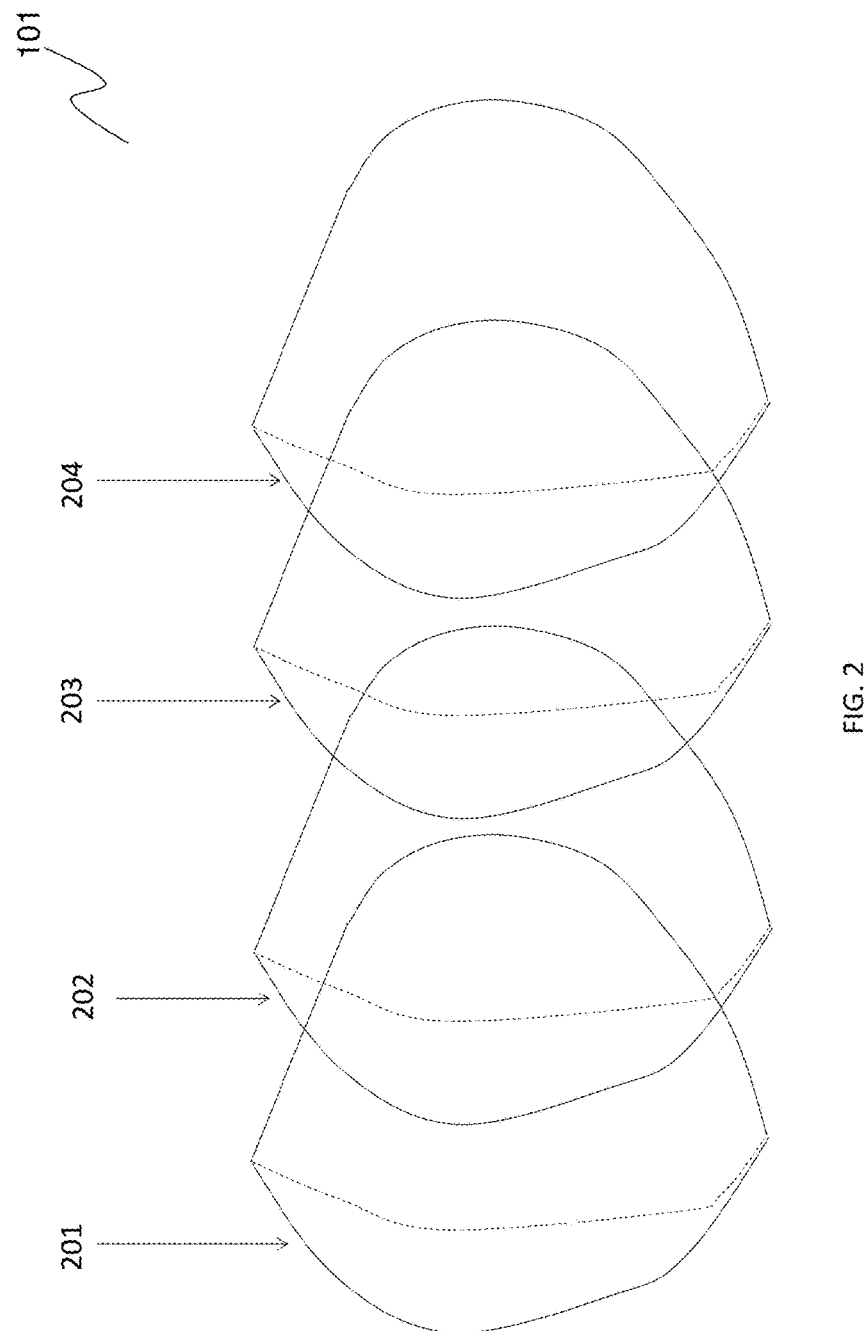
FIG. 2 is a schematic diagram showing different layers of a protective mask.

FIG. 2 illustrates the basic structure of the main body of the present protective mask. The layer distal to the face (201) and the layer proximal to the face (204) are nonwoven layers comprising spunbond polypropylene microfibers. One of these layers (201, 204) is a nonwoven layer comprising antistatic spunbond polypropylene microfibers with a coating comprising electrospun fibers. The coating can be composed of microfibers, submicron fibers, partially gelled submicron fibers interweaved with nanofibers, or the combination thereof. The fibrous coating can bear electrostatic charges. The coating is applied to one side of the nonwoven layer (201, 204) such that the coating is not exposed to the environment outside the protective mask. The electrospun fibers (including eletrospun microfibers and eletrospun nanofibers) of said coating can be polymer fibers or biocide-loaded polymer fibers. Between the layer 201 and layer 204 are two middle layers (202 and 203). The second or third layer (202, 203) is a nonwoven layer comprising meltblown polypropylene microfibers. In other embodiment, one of the second and third layers can be omitted. A stiffening member such as a metal strip or a plastic strip is attached to the upper edge of the main body to conform the face when wearing the protective mask. Preferably, a spongy strip is attached to the inner part of the main body to further improve the face seal when the wearer is wearing the protective mask.

The biocide can include but not limited to silver, copper, CuO, TiO, ZnO, iodine, triclosan and chlorhexidine. The biocide can be encapsulated into the electrospun fibers. The biocide can also be surface-attached onto the electrospun fibers. The biocide can be encapsulated into and surface-attached onto the electrospun fibers. The biocide can be physically trapped by the electrospun fibers. The biocide can also be chemically crosslinked to the electrospun fibers. The biocide can also be blended with the electrospun fibers. The biocide-loaded polymer fibers can contain 0.5%-60% weight/weight (w/w) biocides, such as about 2%-50% (w/w) biocides, with respect to the polymer.

Figure 3:
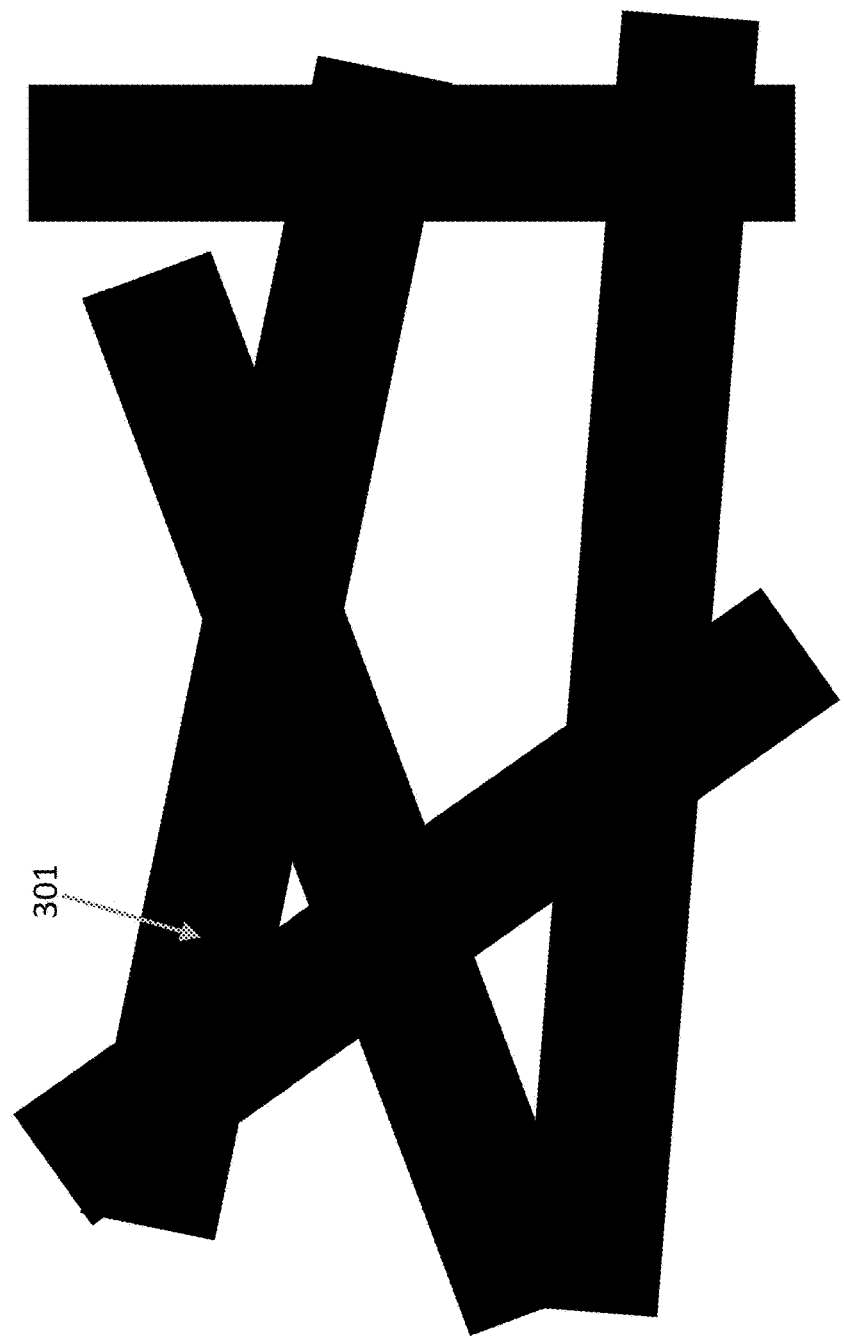
FIG. 3 is a coating comprising microfibers.
Figure 4:
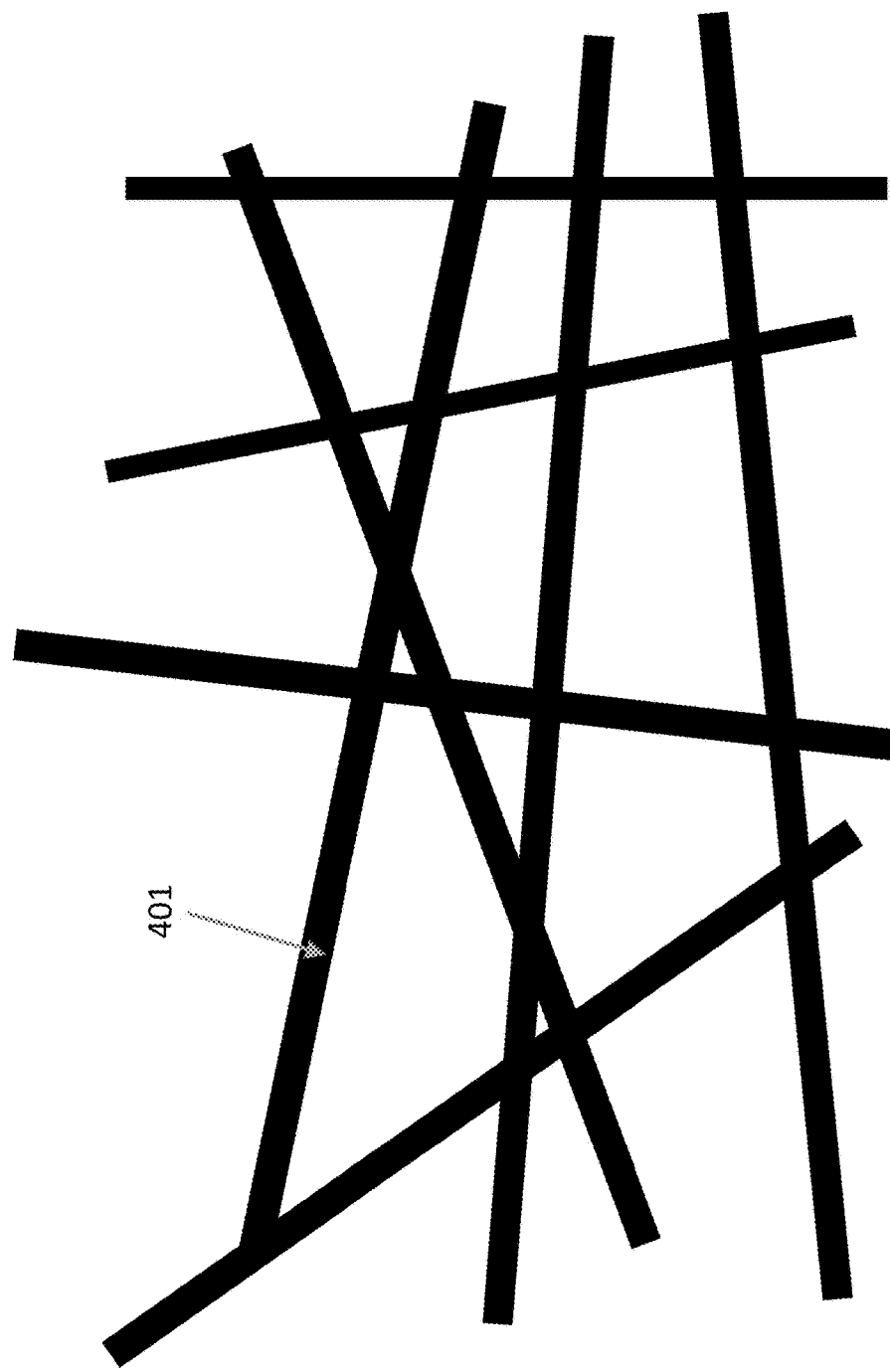
FIG. 4 is a coating comprising submicron fibers.
Figure 5:
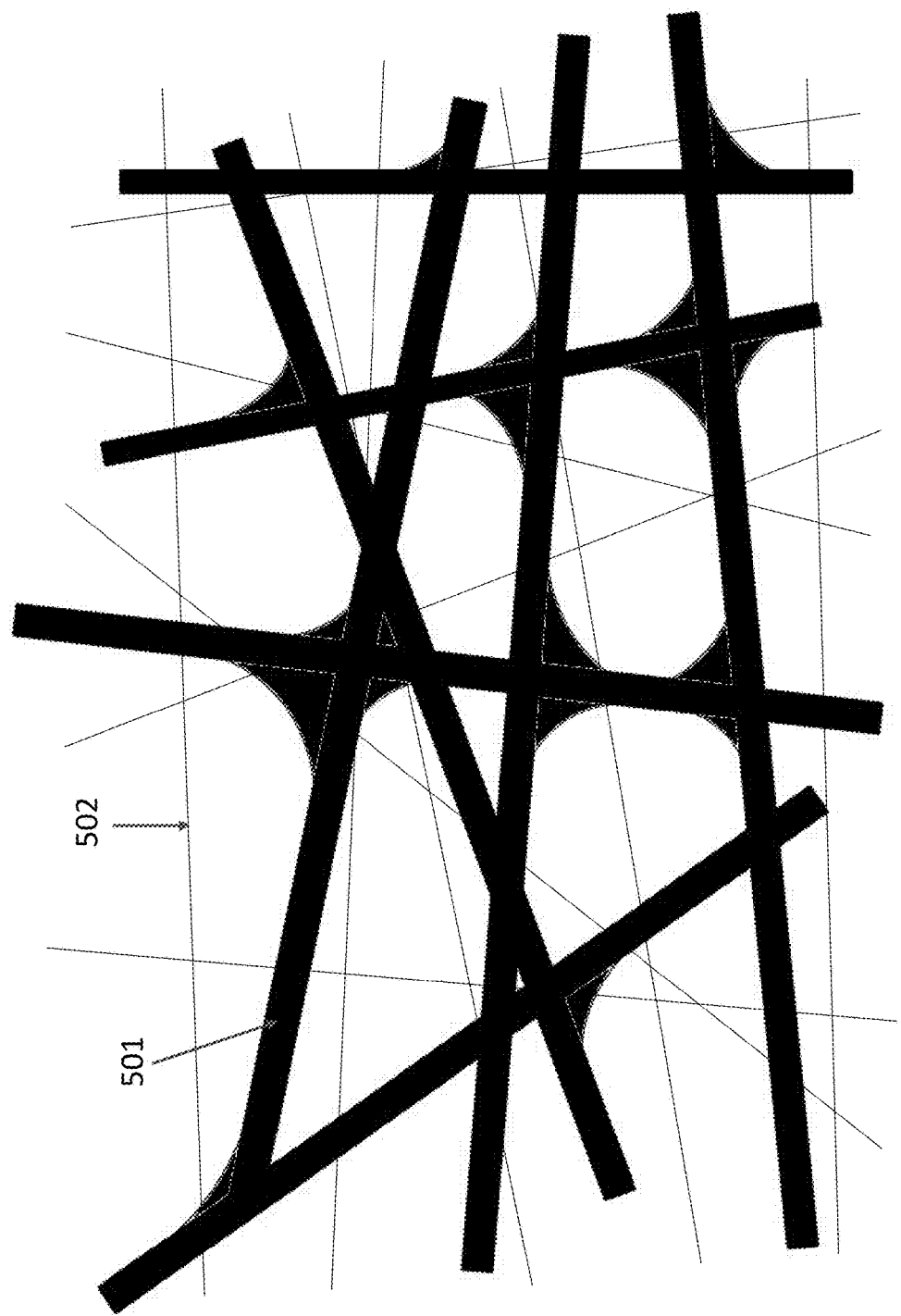
FIG. 5 is a coating comprising partially gelled submicron fibers interweaved with nanofibers.

In an example, the present invention provides electrospun fibers, and electrospun fibrous coating made from a plurality of polymer microfibers, polymer nanofibers, biocide-loaded polymer microfibers, biocide-loaded polymer nanofibers, and any combination thereof. The polymer used to form different types of polymer microfibers, submicron fibers and nanofibers of the present invention can include synthetic polymers such as cellulose acetate (CA), polyamide 6 (PA 6), polystyrene (PS), polyacrylonitrile (PAN), polyvinylpyrrolidone (PVP), polyvinyl alcohol (PVA), poly(lactic acid) (PLA), poly(lactic-co-glycolic acid) (PLGA), polybutylene terephthalate (PBT) and polyurethane (PU). The polymer can also include natural polymers such as gelatin, chitosan and polyhydroxybutyrate-co-hydroxyvalerate (PHBV). The fibrous coating can be composed of electrospun microfibers (301) (FIG. 3), electrospun submicron fibers (401) (FIG. 4), electrospun partially gelled submicron fibers (501) interweaved with electrospun nanofibers (502) (FIG. 5), or any combination thereof.

When the fibrous coating comprising electrospun microfibers is used in a protective mask, the coating has to be very thick in order to achieve N95 level of protection because the inter-fiber pores between microfibers are very large and the surface area-to-volume ratio of the coating is very low when compared with submicron fibers or nanofibers. The thick microfibrous coating improves the filtration efficiency at the expense of breathability.

When the fibrous coating comprising electrospun submicron fibers is used in a protective mask, the required surface density of the coating for achieving N95 level of protection is reduced when compared with the fibrous coating comprising electrospun microfibers because of the smaller inter-fiber pore size and the higher surface area-to-volume ratio. However, the submicron fibers collapse when stacking on each other, thus undermining the breathability.

When the fibrous coating comprising charge-bearing electrospun submicron fibers is used in a protective mask, the required surface density of the coating for achieving N95 level of protection is further reduced when compared with the fibrous coating comprising electrospun submicron fibers without retained charges because particles can be trapped by the charge-bearing fibers due to electrostatic attraction.

When the fibrous coating comprising electrospun partially gelled submicron fibers interweaved with electrospun nanofibers is used in a protective mask, the partially gelled submicron fibers serve as a scaffolding support to prevent the nanofibers from collapsing, thus reducing the inter-fiber pore size and increasing the surface area-to-volume ratio of the coating without increasing the fiber density significantly. This structure can achieve N95 level of protection at a higher breathability, when compared with the coating comprising microfibers or submicron fibers.

When the fibrous coating comprising charge-bearing electrospun partially gelled submicron fibers interweaved with charge-bearing electrospun nanofibers is used in a protective mask, the protective mask can achieve N95 level of protection at a higher breathability, when compared with the protective mask having the same structure without retained charges. A possible reason is that charge-bearing fibers can trap particles by electrostatic attraction, which is an additional particle-trapping mechanism that is not available for the fibers without retained charges. Due to this additional mechanism, the thickness, and hence the air resistance, of the charge-bearing coating can be reduced while maintaining the same level of protection.

The fibrous coating described above can be formed using free-surface electrospinning and methods that can provide for free-surface electrospinning of fibrous coating comprising microfibers, submicron fibers, partially gelled submicron fibers interlaced with nanofibers, or the combination thereof.

Figure 6:
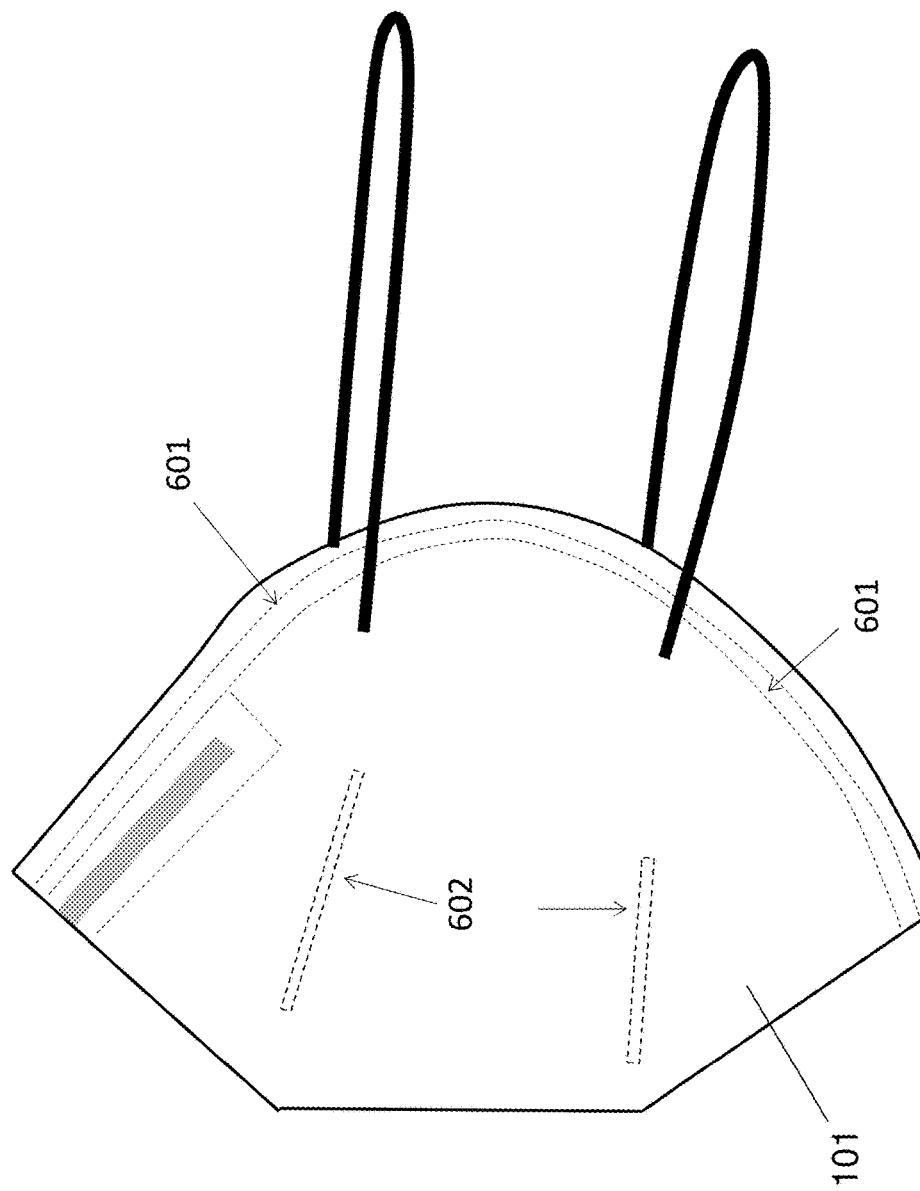
FIG. 6 illustrates the welding parts of the main body of the protective mask.

FIG. 6 illustrates the welding parts of the main body of the protective mask. The melting point of the material to be welded is 170° C. or below. The peripheral part of the main body (601) is welded such that different layers are attached together into one single piece. Four straight lines at the centre of the main body (602) are also welded such that the layer proximal to the face would not be sucked to the face during inhalation.

Description of the Layer Comprising the Spunbond Polypropylene Microfibers

The sheet resistance of the spunbond polypropylene microfibers without antistatic treatment in layer 201 or layer 204 is $10^{10}$-$10^{12}$ Ω/sq, such as about $10^{11}$ Ω/sq. The sheet resistance of the antistatic spunbond polypropylene microfibers in layer 201 or layer 204 is $10^{6}$-$10^{8}$ Ω/sq, such as about $10^{7}$ Ω/sq.

The surface potential of the spunbond polypropylene microfibers without antistatic treatment in layer 201 or layer 204 is 5-10 V, such as about 7-8 V. The surface potential of the antistatic spunbond polypropylene microfibers in layer 201 or layer 204 is 0-5 V, such as about 2-3 V.

The average diameter of the spunbond polypropylene microfibers without antistatic treatment in layer 201 or layer 204 is 10-30 µm, such as about 20 µm. The average diameter of the antistatic spunbond polypropylene microfibers in layer 201 or layer 204 is 10-30 µm, such as about 20 µm.

The surface density of the layer comprising the spunbond polypropylene microfibers without antistatic treatment in layer 201 or layer 204 is 20-50 g/m$^2$, such as about 30 g/m$^2$. The surface density of the layer comprising the antistatic spunbond polypropylene microfibers in layer 201 or layer 204 is 20-50 g/m$^2$, such as about 30 g/m$^2$.

The thickness of the layer comprising the spunbond polypropylene microfibers without antistatic treatment in layer 201 or layer 204 is 0.2-1.5 mm, such as about 0.4-0.6 mm. The thickness of the layer comprising the spunbond polypropylene microfibers without antistatic treatment in layer 1 or layer 4 is 0.2-1.5 mm, such as about 0.4-0.6 mm.

Description of the Coating Comprising Electrospun Fibers

The sheet resistance of the coating comprising electrospun microfibers is $10^{10}$-$10^{12}$ Ω/sq, such as about $10^{11}$ Ω/sq. The sheet resistance of the coating comprising electrospun submicron fibers is $10^{10}$-$10^{12}$ Ω/sq, such as about $10^{11}$ Ω/sq. The sheet resistance of the coating comprising partially gelled electrospun submicron fibers interweaved with electrospun nanofibers is $10^{10}$-$10^{12}$ Ω/sq, such as about $10^{11}$ Ω/sq.

The surface potential of the coating comprising charge-bearing electrospun fibers is 20-60 V, such as about 30-50 V. Charge-bearing electrospun fibers can be made from hydrophobic polymers such as PHBV, PBT, PLA and PLGA. The surface potential of the coating comprising electrospun fibers without retained electrostatic charges is 0-5 V, such as about 2-3 V. Electrospun fibers without retained charges can be made from polar polymers such as polyamide 6, gelatin, chitosan and PU.

The average diameter of the electrospun microfibers is 1-10 µm, such as about 5 µm. The average diameter of the electrospun submicron fibers is 100-999 nm, such as about 300-500 nm. The average diameter of the charge-bearing electrospun submicron fibers is 100-999 nm, such as about 300-500 nm. The average diameter of the partially gelled electrospun submicron fibers is 100-999 nm, such as about 300-500 nm. The average diameter of the nanofibers interweaved with the partially gelled electrospun submicron fibers is 10-99 nm, such as about 40-60 nm. The average diameter of the partially gelled charge-bearing electrospun submicron fibers is 100-999 nm, such as about 300-500 nm. The average diameter of the charge-bearing nanofibers interweaved with the partially gelled charge-bearing electrospun submicron fibers is 10-99 nm, such as about 40-60 nm.

The surface density of the coating comprising electrospun microfibers is 0.08-0.15 g/m$^2$, such as about 0.1-0.13 g/m$^2$. The surface density of the coating comprising electrospun submicron fibers is 0.05-0.11 g/m$^2$, such as about 0.06-0.1 g/m$^2$. The surface density of the coating comprising charge-bearing electrospun submicron fibers is 0.03-0.09 g/m$^2$, such as about 0.04-0.08 g/m$^2$. The surface density of the coating comprising partially gelled electrospun submicron fibers interweaved with electrospun nanofibers is 0.01-0.07 g/m$^2$, such as about 0.02-0.05 g/m$^2$. The surface density of the coating comprising partially gelled charge-bearing electrospun submicron fibers interweaved with charge-bearing electrospun nanofibers is 0.008-0.05 g/m$^2$, such as about 0.01-0.03 g/m$^2$.

The thickness of the coating comprising electrospun microfibers is 200-250 µm, such as about 210-240 µm. The thickness of the coating comprising electrospun submicron fibers is 80-120 µm, such as about 90-110 µm. The thickness of the coating comprising charge-bearing electrospun submicron fibers is 60-100 µm, such as about 70-90 µm. The thickness of the coating comprising partially gelled electrospun submicron fibers interweaved with electrospun nanofibers is 40-80 µm, such as about 50-70 µm. The thickness of the coating comprising partially gelled charge-bearing electrospun submicron fibers interweaved with charge-bearing electrospun nanofibers is 20-60 µm, such as about 30-50 µm.

When the fibrous coating comprising electrospun microfibers is used in a protective mask, the coating has to be very thick (200-250 µm) and the surface density of the coating has to be very high (0.08-0.15 g/m$^2$) in order to filter out more than 95% of particles at the MPPS (i.e. N95 level of protection) because the inter-fiber pores between microfibers are very large and the surface area-to-volume ratio of the coating is very low when compared with submicron fibers or nanofibers. The thick microfibrous coating improves the filtration efficiency at the expense of breathability.

When the fibrous coating comprising electrospun submicron fibers is used in a protective mask, the required surface density of the coating for achieving N95 level of protection is reduced (0.05-0.11 g/m$^2$) when compared with the fibrous coating comprising electrospun microfibers because of the smaller inter-fiber pore size and the higher surface area-to-volume ratio. However, the submicron fibers collapse when stacking on each other, thus still undermining the breathability.

When the fibrous coating comprising electrospun charge-bearing submicron fibers is used in a protective mask, the required surface density of the coating for achieving N95 level of protection is further reduced (0.03-0.09 g/m$^2$) when compared with the fibrous coating comprising electrospun submicron fibers without retained charges because particles can be readily trapped by the charge-bearing fibers by electrostatic attraction.

When the fibrous coating comprising electrospun partially gelled submicron fibers interweaved with electrospun nanofibers is used in a protective mask, the partially gelled submicron fibers serve as a scaffolding support to prevent the submicron fibers and nanofibers from collapsing, thus achieving N95 level of protection without significantly reducing the breathability.

When the fibrous coating comprising charge-bearing electrospun partially gelled submicron fibers interweaved with charge-bearing electrospun nanofibers is used in a protective mask, the required surface density of the coating for achieving N95 level of protection is further reduced (0.008-0.05 g/m$^2$) when compared with the fibrous coating comprising the same fiber structure without retained charges because particles can be readily trapped by the charge-bearing fibers by electrostatic attraction.

Description of the Layer Comprising the Meltblown Polypropylene Microfibers

Between the layer distal to the face (layer 201) and the layer proximal to the face (layer 204) are two middle layers (layer 202 and layer 203). The middle layer (layer 202 or layer 203) is a nonwoven layer comprising meltblown polypropylene microfibers. One of the middle layers (layer 202 or layer 203) can be omitted in some cases.

The sheet resistance of the meltblown polypropylene microfibers is $10^{10}$-$10^{12}$ Ω/sq, such as about $10^{11}$ Ω/sq.

The surface potential of the coating comprising meltblown polypropylene microfibers is 0-5 V, such as about 2 V.

The average diameter of the meltblown polypropylene microfibers is 1-15 µm, such as about 2-4 µm.

The surface density of the layer comprising the meltblown polypropylene microfibers is 20-30 g/m$^2$, such as about 25 g/m$^2$.

The thickness of the layer comprising the meltblown polypropylene microfibers is 0.1-0.5 mm, such as about 0.2-0.4 mm.

A stiffening member such as a metal strip or a plastic strip is attached to the upper edge of the main body to conform the face when wearing the protective mask. The thickness of the metal strip or the plastic strip is 0.5-0.9 mm, such as about 0.7 mm.

Preferably, a spongy strip is attached to the inner part of the main body to further improve the face seal when wearing the protective mask. The distance between the upper edge of the spongy strip and the edge of the main body is 1-2 cm, such as 1.5 cm.

The present disclosure also describes formulations and scalable methods for providing the protective mask described above. More specifically, the present disclosure describes formulations and scalable methods for forming the electrospun fibrous coating on the antistatic nonwoven substrate comprising a plurality of spunbond polypropylene microfibers.

Polymer Solution for Electrospinning

A polymer, such as CA, PA 6, PS, PAN, PVP, PVA, PLA, PLGA, PBT, PU, gelatin, chitosan or PHBV, is dissolved in an appropriate solvent, such as dimethylformamide (DMF), acetic acid (AA), formic acid (FA), dichloromethane (DCM), chloroform, acetone, 1,1,1,3,3,3-hexafluoro-2-propanol (HF2P), trifluoroacetic acid (TFA), 2,2,2-trifluoroethanol (TFE), cyclohexanone, water, or the combination thereof. A biocide, such as silver, copper, CuO, TiO, ZnO, iodine, triclosan and chlorhexidine, is mixed with the polymer solution through gentle stirring and heating using a hotplate magnetic stirrer. The stirring speed is 200-800 rpm, such as about 400-600 rpm. The heating temperature is 25-90° C., such as about 50-80° C. The stirring and heating duration is 1-24 hours, such as about 4-6 hours. The viscosity of the polymer solution is 100-3000 cP, such as about 300-900 cP. The conductivity of the polymer solution is 10-100 µS/cm, such as about 20-40 µS/cm.

Working Conditions for Free-Surface Electrospinning

Fibrous coating is formed by free-surface electrospinning of the polymer solution using the Nanospider (NS1WS500U, Elmarco, Czech Republic) together with a tailor-made external winding and unwinding system. The diameter of the stainless steel collecting electrode (CE) is 0.1-0.3 mm, such as about 0.2 mm The diameter of the stainless steel spinning electrode (SE) is 0.1-0.3 mm, such as about 0.2 mm. The sheet resistance of the antistatic spunbond substrate is $10^6$-$10^8$ Ω/sq, such as about $10^7$ Ω/sq. The distance between the CE and the substrate is 20-30 mm, such as about 25 mm. The distance between the SE and the substrate is 150-200 mm, such as about 190 mm. The applied voltage is 80-100 kV, such as about 90 kV. The current is 0.2-0.7 mA, such as about 0.4-0.5 mA. The temperature is 20-25° C., such as about 21-23° C. The relative humidity is 25-70%, such as about 30-60%. The substrate speed is 1000-3000 mm/min, such as about 2000 mm/min.

EXAMPLES

The embodiments of the present invention can be better understood by reference to the following examples which are offered by way of illustration. The present invention is not limited to the examples given herein.

Example 1

Preparation of PU/CuO Solution for Forming PU/CuO Microfibers

Polyurethane (PU) was dissolved in a mixture of cyclohexanone and water (cyclohexanone : water=95 : 5 by volume) at a concentration of 12% (w/w) to form a PU solution. CuO was mixed with the PU solution at a concentration of 2% (w/w). The mixture was stirred at 500 rpm for 24 hours at room temperature to form the PU/CuO solution. The viscosity of the polymer solution was 890 cP. The conductivity of the polymer solution was 35 µS/cm.

Fabrication of Coating Comprising Electrospun PU/CuO Microfibers

Fibrous coating was formed on an antistatic spunbond substrate by free-surface electrospinning of the PU/CuO solution using the Nanospider (NS1WS500U, Elmarco, Czech Republic) together with a tailor-made external winding and unwinding system. The diameter of the stainless steel collecting electrode (CE) was 0.2 mm The diameter of the stainless steel spinning electrode (SE) was 0.2 mm. The sheet resistance of the antistatic spunbond substrate was $10^7$ Ω/sq. The distance between the CE and the substrate was 25 mm. The distance between the SE and the substrate was 190 mm. The applied voltage was 90 kV. The current was 0.5 mA. The temperature was 23° C. The relative humidity was 33%. The substrate speed was 1500 mm/min.

FIG. 7 shows the SEM image of the electrospun PU/CuO microfibers formed by the free-surface electrospinning of the PU/CuO solution in this example. The sheet resistance of the coating comprising electrospun PU/CuO microfibers is $10^{11}$ Ω/sq. The surface potential of the coating comprising PU/CuO microfibers is 2 V. The average diameter of the electrospun PU/CuO microfibers is 2.2 µm. The surface density of the coating comprising the electrospun PU/CuO microfibers is 0.12 g/m$^2$. The thickness of the coating comprising the electrospun PU/CuO microfibers is 230 µm.

Protective Masks with the Coating Comprising PU/CuO Microfibers

The antistatic spunbond substrate with the coating comprising the electrospun PU/CuO microfibers (i.e. Layer 201) was assembled with Layer 202, Layer 203, Layer 204 and elastic straps into a protective mask, where layer 204 or 203 is a nonwoven layer comprising meltblown polypropylene microfibers. The performance of this type of protective mask was assessed through two tests, namely, (1) sodium chloride (NaCl) aerosol test and (2) inhalation and exhalation resistance tests.

NaCl Aerosol Test

The NaCl aerosol test was performed to evaluate particulate filter penetration as specified in 42 CFR Part 84 and TEB-APR-STP-0059 for requirements on an N95 respirator. Prior to testing, the protective masks were placed in an environment of 85±5% relative humidity (RH) and 38±2.5° C. for 25±1 hours. The filter tester used in this test was a TSI® CERTITEST® Model 8130 Automated Filter Tester capable of measuring filtration efficiency up to 99.999%. It produces a particle size distribution with a count median diameter of 75±20 nm. The mass median diameter is approximately 260 nm, which is generally regarded as the MPPS. The reservoir was filled with a 2% NaCl solution and the instrument allowed a minimum warm-up time of 30 min. The main regulator pressure was set to 75±5 pounds per square inch (psi). The filter holder regulator pressure was set to approximately 35 psi. The NaCl aerosol generator pressure was set to approximately 30 psi and the make-up airflow rate was set to approximately 70 liters per minute (L/min). The neutralized NaCl test aerosol was verified to be at 25±5° C. and 30±10% RH. The NaCl concentration of the test aerosol was determined in mg/m$^3$ by a gravimetric method prior to the load test assessment. The entire protective mask was mounted on a test fixture, placed into the test article holder, and the NaCl aerosol passed through the outside surface of the test article at a continuous airflow rate of 85±4 L/min.

The NIOSH N95 filter efficiency as stated in 42 CFR Part 84.181 is a minimum efficiency for each filter of ≥95%. The average filtration efficiency of the protective masks with the coating comprising electrospun PU/CuO microfibers was 99.889% and none of them possessed filtration efficiency less than 95%, meaning that the protective masks conform to the NIOSH N95 criteria for filter efficiency.

Inhalation and Exhalation Resistance Tests

The tests were performed to evaluate the differential pressure of protective masks in accordance with 42 CFR Part 84.180. The air exchange differential or breathability of protective masks was measured for inhalation resistance using NIOSH procedure TEB-APR-STP-0007 and exhalation resistance with NIOSH procedure TEB-APR-STP-0003. The differential pressure technique is a simple application of a basic physical principle employing a water manometer differential upstream and downstream of the test material, at a constant flow rate. A complete protective mask was mounted to a test fixture comprised of a metal plate with an approximate 3.5 inch diameter hole in the center to allow airflow to reach the mask. The sample holder was assembled by placing a Plexiglas collar around the test fixture and topping with another metal disc with a 3.5 inch opening in the center. The sample holder is held tightly together with clamps and connected to an air source. The manometer is attached to the sample holder by a connection port on the Plexiglas collar. Before testing, the manometer was zeroed and the back pressure in the sample holder checked and verified to be negligible. Resistance measurements were taken with a manometer capable of measuring at least 6 inches of water. For inhalation testing, a negative airflow (vacuum) was applied. For exhalation testing, a positive airflow (compressed air) was used. Airflow was passed through the sample holder at approximately 85±2 L/min.

The inhalation resistance criteria as stated in 42 CFR Part 84.180 is an initial inhalation not exceeding 35 mm water column height pressure (mm H$_2$O). The exhalation resistance criteria as stated in 42 CFR Part 84.180 is an initial exhalation not exceeding 25 mm $H_2O$. The average inhalation resistance of the protective masks with the coating comprising electrospun PU/CuO microfibers was 9.3 mm $H_2O$ and none of them exceeded 35 mm $H_2O$ while the average exhalation resistance of the protective masks with the coating comprising electrospun PU/CuO microfibers was 9.9 mm $H_2O$ and none of them exceeded 25 mm $H_2O$, meaning that the protective masks conform to this NIOSH criterion for airflow resistance.

Example 2

Preparation of PU/CuO Solution for Forming PU/CuO Submicron fibers

PU was dissolved in a mixture of cyclohexanone and water (cyclohexanone: water=95 : 5 by volume) at a concentration of 7.5% (w/w) to form a PU solution. CuO was mixed with the PU solution at a concentration of 2% (w/w). The mixture was stirred at 500 rpm for 24 hours at room temperature to form the PU/CuO solution. The viscosity of the polymer solution was 330 cP. The conductivity of the polymer solution was 28 μS/cm.

Fabrication of Coating Comprising PU/CuO Submicron Fibers

Fibrous coating was formed on an antistatic spunbond substrate by free-surface electrospinning of the PU/CuO solution using the Nanospider (NS1WS500U, Elmarco, Czech Republic) together with a tailor-made external winding and unwinding system. The diameter of the stainless steel collecting electrode (CE) was 0.2 mm. The diameter of the stainless steel spinning electrode (SE) was 0.2 mm. The sheet resistance of the antistatic spunbond substrate was $10^7$ Ω/sq. The distance between the CE and the substrate was 25 mm. The distance between the SE and the substrate was 190 mm. The applied voltage was 90 kV. The current was 0.5 mA. The temperature was 23° C. The relative humidity was 33%. The substrate speed was 1500 mm/min.

FIG. 8 shows the SEM image of the electrospun PU/CuO submicron fibers. The sheet resistance of the coating comprising electrospun PU/CuO submicron fibers is $10^{11}$ Ω/sq. The surface potential of the coating comprising PU/CuO submicron fibers is 2 V. The average diameter of the electrospun PU/CuO submicron fibers is 890 nm. The surface density of the coating comprising the electrospun PU/CuO submicron fibers is 0.08 $g/m^2$. The thickness of the coating comprising the electrospun PU/CuO submicron fibers is 98 μm.

Protective Masks with the Coating Comprising PU/CuO Submicron Fibers

The substrate with the coating comprising electrospun PU/CuO submicron fibers (i.e. Layer 201) was assembled with Layer 202, Layer 203, Layer 204 and elastic straps into a protective mask, where layer 202 or 203 is a nonwoven layer comprising meltblown polypropylene microfibers. The performance of this type of protective mask was assessed through two tests, namely, (1) sodium chloride (NaCl) aerosol test and (2) inhalation and exhalation resistance tests.

NaCl Aerosol Test

The NaCl aerosol test was conducted as described in Example 1.

The average filtration efficiency of the protective masks with the coating comprising electrospun PU/CuO submicron fibers was 99.862% and none of them possessed filtration efficiency less than 95%, meaning that the protective masks conform to the NIOSH N95 criteria for filter efficiency.

Inhalation and Exhalation Resistance Tests

The inhalation and exhalation resistance tests were conducted as described in Example 1.

The average inhalation resistance of the protective masks with the coating comprising electrospun PU/CuO submicron fibers was 8.1 mm $H_2O$ and none of them exceeded 35 mm $H_2O$ while the average exhalation resistance of the protective masks with the coating comprising electrospun PU/CuO submicron fibers was 7.9 mm $H_2O$ and none of them exceeded 25 mm $H_2O$, meaning that the protective masks conform to this NIOSH criterion for airflow resistance.

Example 3

Preparation of PHBV/CuO Solution for Forming PHBV/CuO Submicron Fibers

PHBV was dissolved in 2,2,2-trifluoroethanol at a concentration of 5% (w/w). CuO was mixed with the PHBV solution at a concentration of 2% (w/w). The mixture was stirred at 300 rpm for 5 hours at 50° C. to form the PHBV/CuO solution. The viscosity of the polymer solution was 230 cP. The conductivity of the polymer solution was 38 μS/cm.

Fabrication of Coating Comprising PHBV/CuO Submicron Fibers

Fibrous coating was formed on an antistatic spunbond substrate by free-surface electrospinning of the PHBV/CuO solution using the Nanospider (NS1WS500U, Elmarco, Czech Republic) together with a tailor-made external winding and unwinding system. The diameter of the stainless steel collecting electrode (CE) was 0.2 mm. The diameter of the stainless steel spinning electrode (SE) was 0.2 mm. The sheet resistance of the antistatic spunbond substrate was $10^7$ Ω/sq. The distance between the CE and the substrate was 25 mm. The distance between the SE and the substrate was 190 mm. The applied voltage was 90 kV. The current was 0.5 mA. The temperature was 22° C. The relative humidity is 32%. The substrate speed was 2000 mm/min.

Figure 9:
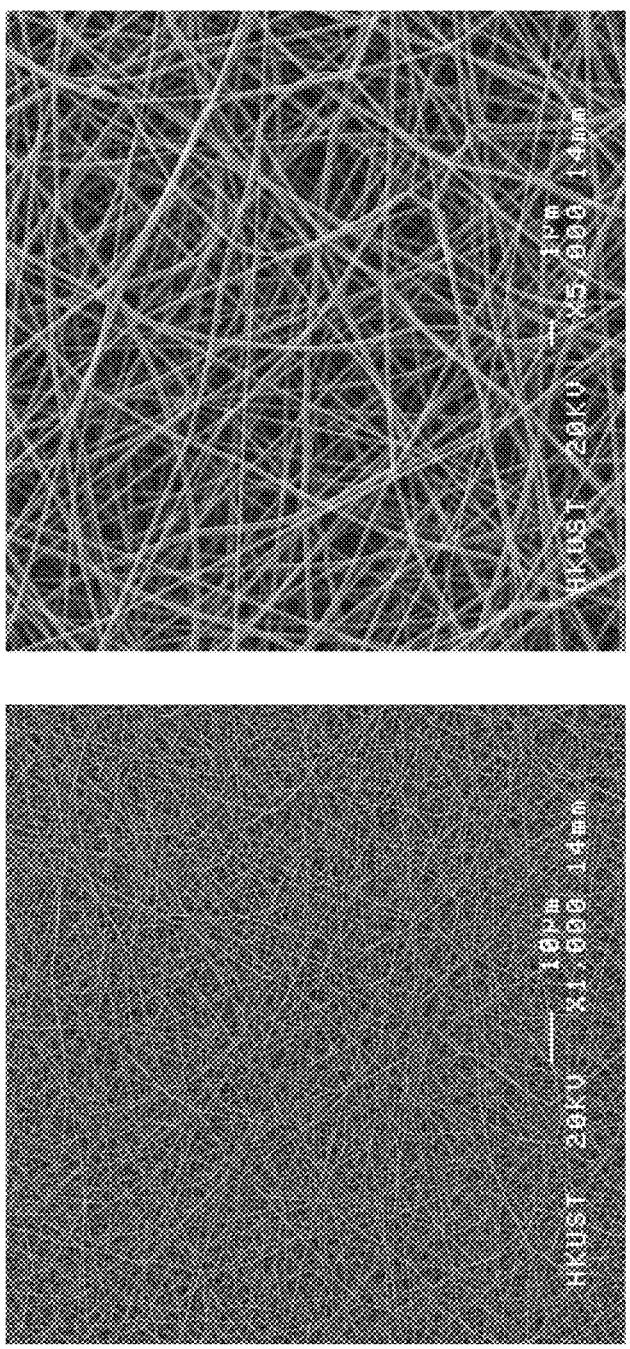
FIG. 9 shows the SEM image of electrospun PHBV/CuO submicron fibers.

FIG. 9 shows the SEM image of the electrospun PHBV/CuO submicron fibers. The sheet resistance of the coating comprising electrospun PHBV/CuO submicron fibers is $10^{11}$ Ω/sq. The surface potential of the coating comprising PU/CuO submicron fibers is 45 V. The average diameter of the electrospun PHBV/CuO submicron fibers is 260 nm. The surface density of the coating comprising the electrospun PHBV/CuO submicron fibers is 0.05 $g/m^2$. The thickness of the coating comprising the electrospun PHBV/CuO submicron fibers is 82 μm.

Protective Masks with the Coating Comprising PHBV/CuO Submicron Fibers

The substrate with the coating comprising electrospun PHBV/CuO submicron fibers (i.e. Layer 201) was assembled with Layer 202, Layer 203, Layer 204 and elastic straps into a protective mask. The performance of this type of protective mask was assessed through two tests, namely, (1) sodium chloride (NaCl) aerosol test and (2) inhalation and exhalation resistance tests.

NaCl Aerosol Test

The NaCl aerosol test was conducted as described in Example 1.

The average filtration efficiency of the protective masks with the coating comprising electrospun PHBV/CuO submicron fibers was 99.812% and none of them possessed filtration efficiency less than 95%, meaning that the protective masks conform to the NIOSH N95 criteria for filter efficiency.

Inhalation and Exhalation Resistance Tests

The inhalation and exhalation resistance tests were conducted as described in Example 1.

The average inhalation resistance of the protective masks with the coating comprising electrospun PHBV/CuO submicron fibers was 7.3 mm $H_2O$ and none of them exceeded 35 mm $H_2O$ while the average exhalation resistance of the protective masks with the coating comprising electrospun PHBV/CuO submicron fibers was 8.1 mm $H_2O$ and none of them exceeded 25 mm $H_2O$, meaning that the protective masks conform to this NIOSH criterion for airflow resistance.

Example 4

Preparation of PU/CuO Solution for Forming PU/CuO Submicron Fibers or Nanofibers PU/CuO solution was prepared as described in Example 2.

Fabrication of Coating Comprising Partially Gelled PU/CuO Submicron Fibers Interweaved with PU/CuO Nanofibers Fibrous coating was formed on an antistatic spunbond substrate by free-surface electrospinning as described in Example 2 except that the relative humidity was 58% and the substrate speed was 2700 mm/min. The purpose of increasing the relative humidity was to reduce the evaporation rate of the solvent during electrospinning such that part of the electrospun jet was not completely solidified before reaching the substrate, thus leaving the partially jelled fibrous structures among the submicron fibers. The portions between the partially jelled portions became nanofibers due to stretching of the polymer solution to the partially jelled portions. Since increasing the substrate speed can reduce the thickness of the coating, it is not necessary to form a very thick coating to achieve N95 level of protection due to the presence of the nanofibers interweaved with the partially gelled submicron fibers.

Figure 10:
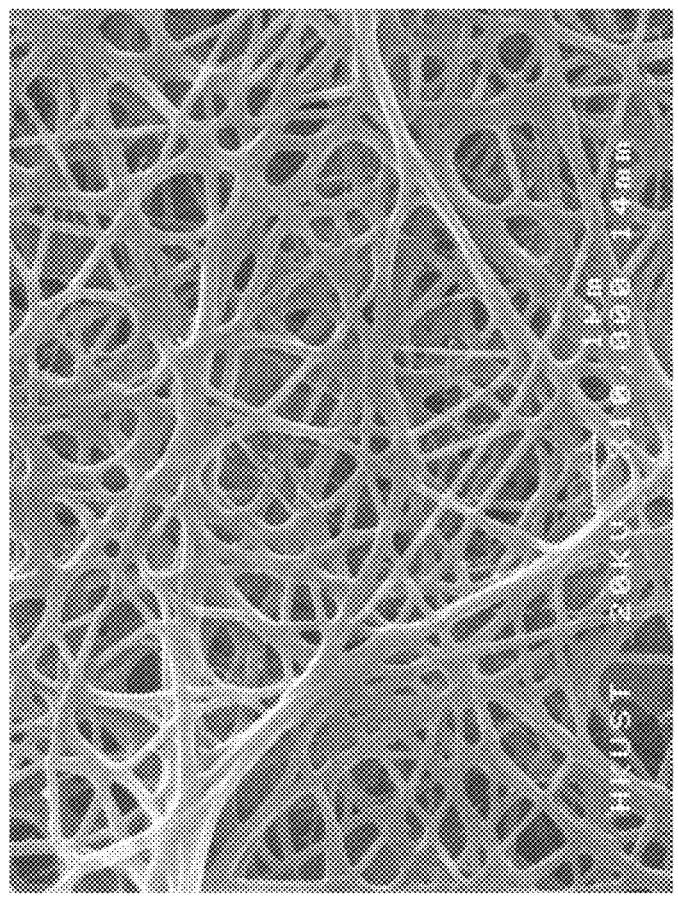
FIG. 10 shows the SEM image of electrospun partially gelled PU/CuO submicron fibers interweaved with PU/CuO nanofibers.

FIG. 10 shows the SEM image of the electrospun partially gelled PU/CuO submicron fibers interweaved with PU/CuO nanofibers. The sheet resistance of the coating comprising electrospun partially gelled PU/CuO submicron fibers interweaved with PU/CuO nanofibers was $10^{12}$ Ω/sq. The surface potential of the coating comprising electrospun partially gelled PU/CuO submicron fibers interweaved with PU/CuO nanofibers was 2 V. The average diameter of the electrospun partially gelled PU/CuO submicron fibers was 320 nm. The average diameter of the electrospun PU/CuO nanofibers interweaved with the partially gelled PU/CuO submicron fibers was 85 nm. The surface density of the coating comprising the electrospun partially gelled PU/CuO submicron fibers interweaved with PU/CuO nanofibers was 0.04 g/m². The thickness of the coating comprising the electrospun partially gelled PU/CuO submicron fibers interweaved with PU/CuO nanofibers was 63 μm.

Protective Masks with the Coating Comprising Partially Gelled PU/CuO Submicron Fibers Interweaved with PU/CuO Nanofibers The substrate with the coating comprising electrospun partially gelled PU/CuO submicron fibers interweaved with PU/CuO nanofibers (i.e. Layer 1) was assembled with Layer 2, Layer 3, Layer 4 and elastic straps into a protective mask. The performance of this type of protective mask was assessed through two tests, namely, (1) sodium chloride (NaCl) aerosol test and (2) inhalation and exhalation resistance tests.

NaCl Aerosol Test

The NaCl aerosol test was conducted as described in Example 1.

The average filtration efficiency of the protective masks with the coating comprising electrospun partially gelled PU/CuO submicron fibers interweaved with PU/CuO nanofibers was 99.862% and none of them possessed filtration efficiency less than 95%, meaning that the protective masks conform to the NIOSH N95 criteria for filter efficiency.

Inhalation and Exhalation Resistance Tests

The inhalation and exhalation resistance tests were conducted as described in Example 1.

The average inhalation resistance of the protective masks with the coating comprising electrospun partially gelled PU/CuO submicron fibers interweaved with PU/CuO nanofibers was 7.2 mm $H_2O$ and none of them exceeded 35 mm $H_2O$ while the average exhalation resistance of the protective masks with the coating comprising electrospun partially gelled PU/CuO submicron fibers interweaved with PU/CuO nanofibers was 7.8 mm $H_2O$ and none of them exceeded 25 mm $H_2O$, meaning that the protective masks conform to this NIOSH criterion for airflow resistance.

Example 5

Preparation of PHBV/CuO Solution Forming PHBV/CuO Submicron Fibers or Nanofibers PHBV/CuO solution was prepared as described in Example 3.

Fabrication of Coating Comprising Partially Gelled PHBV/CuO Submicron Fibers Interweaved with PHBV/CuO Nanofibers Fibrous coating was formed on an antistatic spunbond substrate by free-surface electrospinning as described in Example 4 except that the substrate speed was further increased to 3000 mm/min. The purpose of increasing the substrate speed was to reduce the thickness of the coating because it was not necessary to form a very thick coating to achieve N95 level of protection due to the charge-bearing ability of the PHBV/CuO fibers, which enhanced particles trapping by electrostatic attraction.

Figure 11:
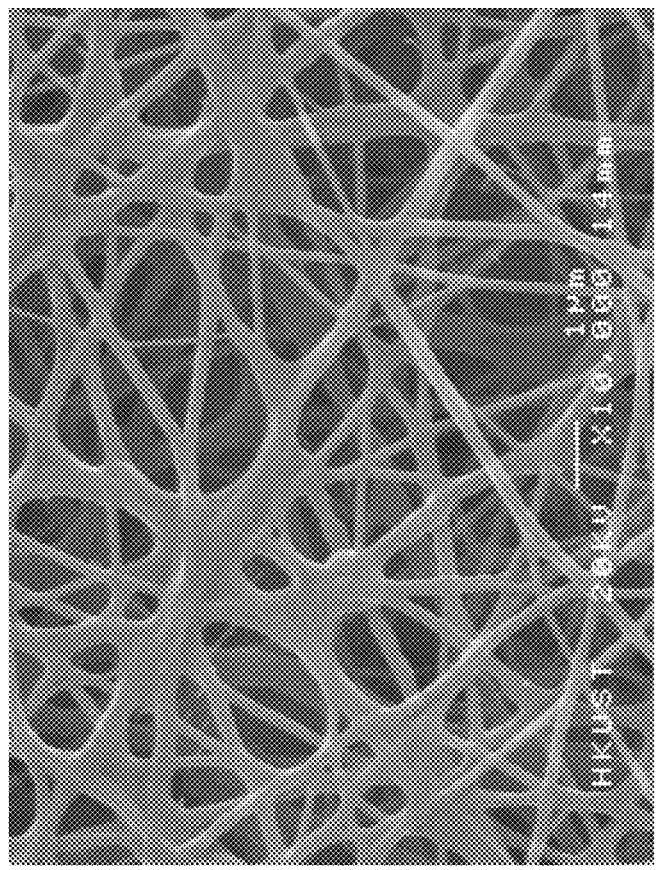
FIG. 11 shows the SEM image of electrospun partially gelled PHBV/CuO submicron fibers interweaved with PHBV/CuO nanofibers.

FIG. 11 shows the SEM image of the electrospun partially gelled PHBV/CuO submicron fibers interweaved with PHBV/CuO nanofibers. The sheet resistance of the coating comprising electrospun partially gelled PHBV/CuO submicron fibers interweaved with PHBV/CuO nanofibers was $10^{11}$ Ω/sq. The surface potential of the coating comprising electrospun partially gelled PHBV/CuO submicron fibers interweaved with PHBV/CuO nanofibers was 55 V. The average diameter of the electrospun partially gelled PHBV/CuO submicron fibers was 410 nm. The average diameter of the electrospun PHBV/CuO nanofibers interweaved with the partially gelled PHBV/CuO submicron fibers was 72 nm. The surface density of the coating comprising the electrospun partially gelled PHBV/CuO submicron fibers interweaved with PHBV/CuO nanofibers was 0.02 g/m². The thickness of the coating comprising the electrospun partially gelled PHBV/CuO submicron fibers interweaved with PHBV/CuO nanofibers was 37 μm.

Protective Masks with the Coating Comprising Partially Gelled PHBV/CuO Submicron Fibers Interweaved with PHBV/CuO Nanofibers The substrate with the coating comprising electrospun partially gelled PHBV/CuO submicron fibers interweaved with PHBV/CuO nanofibers (i.e. Layer 201) was assembled with Layer 202, Layer 203, Layer 204 and elastic straps into a protective mask. The performance of this type of protective mask was assessed through three tests, namely, (1) sodium chloride (NaCl) aerosol test, (2) inhalation and exhalation resistance tests, and (3) antimicrobial tests.

NaCl Aerosol Test

The NaCl aerosol test was conducted as described in Example 1.

The average filtration efficiency of the protective masks with the coating comprising electrospun partially gelled PHBV/CuO submicron fibers interweaved with PHBV/CuO nanofibers was 95.97% and none of them possessed filtration efficiency less than 95%, meaning that the protective masks conform to the NIOSH N95 criteria for filter efficiency.

Inhalation and Exhalation Resistance Tests

The inhalation and exhalation resistance tests were conducted as described in Example 1.

The average inhalation resistance of the protective masks with the coating comprising electrospun partially gelled PHBV/CuO submicron fibers interweaved with PHBV/CuO nanofibers was 5.4 mm $H_2O$ and none of them exceeded 35 mm $H_2O$ while the average exhalation resistance of the protective masks with the coating comprising electrospun partially gelled PHBV/CuO submicron fibers interweaved with PHBV/CuO nanofibers was 5.6 mm $H_2O$ and none of them exceeded 25 mm $H_2O$, meaning that the protective masks conform to this NIOSH criterion for airflow resistance.

Antimicrobial Tests

The antimicrobial tests consisted of inoculating uniform pieces of the test material with the test organism(s), then determining the percent reduction of the test organism(s) after specified exposure periods.

Tubes of soybean casein digest broth (SCDB) media were inoculated with stock cultures of bacteria and incubated at 35-39° C. for 2-5 days. The cultures were vortexed to remove clumps and the concentration was adjusted to the appropriate challenge level.

The protective masks with different coatings prepared according to the examples described hereinabove were cut into 48×48±1 mm swatches. All tests were performed in three replicates for each type of the protective masks. A 0.1 mL aliquot of the test culture was added to each sample and positive control. The inoculum was vortexed frequently to ensure uniform distribution of challenge. The test swatches were held at room temperature for the designated time intervals. At time 1, 3, and 5 minutes the test articles were extracted by removing the test sample from the containers and placing them into 100 mL bottles containing neutralizer broth. The bottles were shaken manually for one minute or 100 times in a 12 inch path to extract surviving organism.

The extract fluid from all test article extraction bottles was tested for viable organisms. All plating was performed in triplicate using a standard spread plate method. Bacterial test articles were plated onto SCDA and incubated at 37±2° C. for 2-5 days.

A positive control was performed by testing sterile gauze in the same manner as the test article. A negative control was tested by plating aliquots from a sterile 100 mL bottle of neutralizer broth onto the appropriate media in triplicate.

Organism counts represent the number of organism per specimen article. The percent reduction for organism was calculated by the test article treatment as follows $$R = \frac{100(C-S)}{C}$$

where

R=% reduction

C=Average number of organisms recovered from the inoculated untreated control at 0 hour S=Average number of organisms recovered from the inoculated treated test article after exposure for the desired contact period The protective mask sample from Example 5 exhibited 99.72%, 93%, and 60% reduction of *Staphylococcus aureus* (ATCC #6538) within 5 minutes, 3 minutes, and 1 minute, respectively.

The protective mask sample from Example 5 exhibited 99.9919%, 99.9927%, and 99.9927% reduction of *Pseudomonas aeruginosa* (ATCC #9027) within 5 minutes, 3 minutes, and 1 minute, respectively.

What is claimed is:

1. A protective mask comprising an ultrafine fibrous coating on a first microfibrous substrate, said ultrafine fibrous coating comprising: partially gelled submicron fibers interweaved with nanofibers; and a biocide which is encapsulated into, surface-attached onto, blended with, physically trapped, or chemically linked to said submicron fibers and nanofibers.

2. The protective mask of claim 1, further comprising: one or more subsequent layers of microfibrous substrates attached to said first microfibrous substrate by ultrasonic welding.

3. The protective mask of claim 2, wherein said protective mask has a filtration efficiency of 95-99.999% in a sodium chloride aerosol test at an airflow rate of around 85 L/min, wherein the sodium chloride aerosol has sodium chloride particles with a mass median diameter of approximately 260 nm.

4. The protective mask of claim 2, wherein said protective mask has an inhalation resistance of 5-10 mm $H_2O$ at an airflow rate of around 85 L/min.

5. The protective mask of claim 2, wherein said protective mask has an exhalation resistance of 5-10 mm $H_2O$ at an airflow rate of around 85 L/min.

6. The protective mask of claim 2, wherein said protective mask exhibits over 99% reduction of bacteria within 5 minutes for gram-positive bacteria comprising *Staphylococcus aureus*.

7. The protective mask of claim 2, wherein said protective mask exhibits over 99% reduction of bacteria within 5 minutes for gram-negative bacteria comprising *Pseudomonas aeruginosa*.

8. The protective mask of claim 2, wherein said first microfibrous substrate adapted to be distal to a wearer's face and one of said subsequent layers of microfibrous substrate adapted to be proximal to said wearer's face are made of antistatic spunbond microfibers while two of said subsequent layers of microfibrous substrate are made of meltblown microfibers and sandwiched between said first microfibrous substrate adapted to be distal to said wearer's face and said one of the subsequent layers adapted to be proximal to said wearer's face in order to form a main body of said protective mask.

9. The protective mask of claim 8, wherein a peripheral part of the main body is welded such that different layers of said microfibrous substrates are attached together into one while four straight lines at said main body are also welded such that said one of the microfibrous substrate adapted to be proximal to said wearer's face would not be sucked to the wearer's face during inhalation.

10. The protective mask of claim 1, wherein said partially gelled submicron fibers has a diameter of 100-1000 nm.

11. The protective mask of claim 1, wherein said partially gelled submicron fibers comprise a gelled portion with an area of 0.2-1 µm².

12. The protective mask of claim 1, wherein said partially gelled submicron fibers comprise two gelled portions with a distance of 1-10 µm between the two gelled portions.

13. The protective mask of claim 1, wherein the nanofibers has a diameter of 10-99 nm.

14. The protective mask of claim 1, wherein the nanofibers is in weight percentage of 30-50% with respect to the submicron fibers.

15. The protective mask of claim 1, wherein the ultrafine fibrous coating has a surface density of 0.008-0.05 g/m².

16. The protective mask of claim 1, wherein the ultrafine fibrous coating has a thickness of 20-60 µm.

17. The protective mask of claim 1, wherein the ultrafine fibrous coating has a surface potential of 20-60 V.

18. The protective mask of claim 1, wherein the partially gelled submicron fibers and nanofibers are made of polymers comprising cellulose acetate (CA), polyamide 6 (PA 6), polystyrene (PS), polyacrylonitrile (PAN), polyvinylpyrrolidone (PVP), polyvinyl alcohol (PVA), poly(lactic acid) (PLA), poly(lactic-co-glycolic acid) (PLGA), polybutylene terephthalate (PBT), polyurethane (PU), gelatin, chitosan or polyhydroxybutyrate-co-hydroxyvalerate (PHBV).

19. The protective mask of claim 1, wherein the biocide comprises silver, copper, copper oxide (CuO), titanium oxide (TiO), zinc oxide (ZnO), iodine, triclosan and/or chlorhexidine.

20. The protective mask of claim 1, wherein said partially gelled submicron fibers and said nanofibers are made of polymers selected from polyurethane or polyhydroxybutyrate-co-hydroxyvalerate while said biocide is copper oxide.

* * * * *